US012453842B2

(12) United States Patent
Roewer et al.

(10) Patent No.: US 12,453,842 B2
(45) Date of Patent: Oct. 28, 2025

(54) CATHETERS ADAPTED FOR AGENT DELIVERY

(71) Applicant: EMBOLX, INC., Sunnyvale, CA (US)

(72) Inventors: Thomas Roewer, Sunnyvale, CA (US); Michael P. Allen, Los Altos, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

(21) Appl. No.: 18/043,873

(22) PCT Filed: Jun. 29, 2022

(86) PCT No.: PCT/US2022/035545
§ 371 (c)(1),
(2) Date: Mar. 2, 2023

(87) PCT Pub. No.: WO2023/278594
PCT Pub. Date: Jan. 5, 2023

(65) Prior Publication Data

US 2023/0226328 A1 Jul. 20, 2023

Related U.S. Application Data

(60) Provisional application No. 63/202,989, filed on Jul. 2, 2021.

(51) Int. Cl.
*A61M 25/10* (2013.01)
*A61M 25/00* (2006.01)
*A61M 25/09* (2006.01)

(52) U.S. Cl.
CPC .... *A61M 25/1018* (2013.01); *A61M 25/0023* (2013.01); *A61M 25/09* (2013.01); *A61M 2025/0042* (2013.01)

(58) Field of Classification Search
CPC ................ A61M 25/104; A61M 25/10; A61M 25/1011; A61M 25/1018;
(Continued)

(56) References Cited

U.S. PATENT DOCUMENTS 3,734,100 A 5/1973 Walker et al.
4,198,981 A 4/1980 Sinnreich
(Continued)

FOREIGN PATENT DOCUMENTS

CN 101400400 A 4/2009
CN 102159277 A 8/2011
(Continued)

OTHER PUBLICATIONS

Angiodynamics; Soft-vu angiographic catheters; 2 pages; retrieved from the internet (http://www.angiodynamics.com/products/soft-vu) on Aug. 17, 2018.
(Continued)

*Primary Examiner* — Kevin C Sirmons
*Assistant Examiner* — Alexandra LaLonde
(74) *Attorney, Agent, or Firm* — Shay Glenn LLP

(57) ABSTRACT

Medical delivery devices, such as catheters, and methods of use and manufacture of the medical delivery devices. The medical delivery devices are adapted to facilitate delivery of an agent into a patient. The medical delivery devices may have one or more deformable lumens, each lumen of the one or more deformable lumens has a collapsed configuration and an open configuration. The medical delivery devices may include one or more agent delivery ports, any agent delivery port of the one or more agent delivery ports may be proximal or distal to an expandable device, such as a balloon.

19 Claims, 14 Drawing Sheets

(58) Field of Classification Search

CPC ...... A61M 25/10181; A61M 25/10184; A61M 25/1027; A61M 25/1034; A61M 25/0023; A61M 25/0009; A61M 25/0015; A61M 25/0021; A61M 25/0026; A61M 25/0028; A61M 25/0029; A61M 25/0032; A61M 25/0051; A61M 25/0052; A61M 25/0053; A61M 25/0054; A61M 25/007; A61M 25/0071; A61M 25/0074; A61M 25/01; A61M 25/0102; A61M 25/09; A61M 25/09041; A61M 2025/0024; A61M 2025/0025; A61M 2025/0035; A61M 2025/0036; A61M 2025/0037; A61M 2025/004; A61M 2025/0042; A61M 2025/0047; A61M 2025/0059; A61M 2025/0177; A61M 2025/1043; A61M 2025/105; A61M 2025/1061; A61M 2025/1063; A61M 2025/1084; A61M 2025/09008; A61M 2025/091; A61M 2025/09116

See application file for complete search history.

(56) References Cited

U.S. PATENT DOCUMENTS 4,545,390 A 10/1985 Leary
4,581,017 A 4/1986 Sahota
4,737,153 A 4/1988 Shimamura et al.
4,748,982 A 6/1988 Horzewski et al.
4,892,519 A 1/1990 Songer et al.
4,896,669 A 1/1990 Bhate et al.
4,898,591 A 2/1990 Jang et al.
4,909,252 A 3/1990 Goldberger
4,944,745 A 7/1990 Sogard et al.
4,976,690 A 12/1990 Solar et al.
4,990,143 A 2/1991 Sheridan
5,000,734 A 3/1991 Boussignac et al.
5,040,548 A 8/1991 Yock
5,045,072 A 9/1991 Castillo et al.
5,047,045 A 9/1991 Arney et al.
5,078,685 A 1/1992 Colliver
5,090,958 A 2/1992 Sahota
5,100,386 A 3/1992 Inoue
5,129,887 A 7/1992 Eutheneuer et al.
5,137,513 A 8/1992 Mcinnes et al.
5,156,594 A 10/1992 Keith et al.
5,217,434 A 6/1993 Arney
5,234,416 A 8/1993 Macaulay et al.
5,254,107 A 10/1993 Soltesz
5,279,562 A 1/1994 Sirhan et al.
5,318,532 A 6/1994 Frassica
5,334,154 A 8/1994 Samson et al.
5,342,386 A 8/1994 Trotta
5,356,388 A 10/1994 Sepetka et al.
5,358,493 A 10/1994 Schweich, Jr. et al.
5,370,655 A 12/1994 Burns
5,380,301 A 1/1995 Prichard et al.
5,423,754 A 6/1995 Cornelius et al.
5,423,829 A 6/1995 Pham et al.
5,429,605 A 7/1995 Richling: Bernd
5,454,795 A 10/1995 Samson
5,470,314 A 11/1995 Walinsky
5,484,409 A 1/1996 Atkinson et al.
5,498,251 A 3/1996 Dalton
5,501,667 A 3/1996 Verduin
5,509,910 A 4/1996 Lunn
5,538,510 A 7/1996 Fontirroche et al.
5,556,383 A 9/1996 Wang et al.
5,582,619 A 12/1996 Ken
5,584,821 A 12/1996 Hobbs et al.
5,588,442 A 12/1996 Scovil et al.
5,599,326 A 2/1997 Carter
5,624,449 A 4/1997 Pham et al.
5,637,086 A 6/1997 Ferguson et al.
5,643,254 A 7/1997 Scheldrup et al.
5,647,198 A 7/1997 Mihailovic
5,649,949 A 7/1997 Wallace et al.
5,658,263 A 8/1997 Dang et al.
5,669,905 A 9/1997 Scheldrup et al.
5,674,198 A 10/1997 Leone
5,690,666 A 11/1997 Berenstein et al.
5,690,667 A 11/1997 Gia
5,718,711 A 2/1998 Berenstein et al.
5,722,424 A 3/1998 Engelson
5,749,837 A 5/1998 Palermo et al.
5,766,192 A 6/1998 Zacca
5,769,830 A 6/1998 Parker
5,775,327 A 7/1998 Randolph et al.
5,792,300 A 8/1998 Inderbitzen et al.
5,797,874 A 8/1998 Spears
5,800,454 A 9/1998 Jacobsen et al.
5,807,355 A 9/1998 Ramzipoor et al.
5,820,592 A 10/1998 Hammerslag
5,830,182 A 11/1998 Wang et al.
5,833,705 A 11/1998 Ken et al.
5,843,032 A 12/1998 Kastenhofer
5,843,050 A 12/1998 Jones et al.
5,851,203 A 12/1998 Van Muiden
5,853,418 A 12/1998 Ken et al.
5,868,704 A 2/1999 Campbell et al.
5,879,324 A * 3/1999 von Hoffmann ... A61M 25/104 604/523
5,891,110 A 4/1999 Larson et al.
5,891,128 A 4/1999 Gia et al.
5,911,717 A 6/1999 Jacobsen et al.
5,938,653 A 8/1999 Pepin
5,951,539 A 9/1999 Nita et al.
5,951,929 A 9/1999 Wilson
5,984,878 A 11/1999 Engelson
5,984,929 A 11/1999 Bashiri et al.
6,013,084 A 1/2000 Ken et al.
6,014,919 A 1/2000 Jacobsen et al.
6,019,757 A 2/2000 Scheldrup
6,022,340 A 2/2000 Sepetka et al.
6,036,670 A 3/2000 Wijeratne et al.
6,036,682 A 3/2000 Lange et al.
6,056,719 A * 5/2000 Mickley .............. A61M 25/104 604/96.01
6,066,157 A 5/2000 Barbere
6,066,667 A 5/2000 Ashbrook
6,068,610 A 5/2000 Ellis et al.
6,071,286 A 6/2000 Mawad
6,090,099 A 7/2000 Samson et al.
6,103,037 A 8/2000 Wilson
6,123,714 A 9/2000 Gia et al.
6,156,061 A 12/2000 Wallace et al.
6,165,163 A 12/2000 Chien et al.
6,187,027 B1 2/2001 Mariant et al.
6,190,358 B1 2/2001 Fitzmaurice et al.
6,190,393 B1 2/2001 Bevier et al.
6,203,547 B1 3/2001 Nguyen et al.
6,258,080 B1 7/2001 Samson
6,270,495 B1 8/2001 Palermo
6,280,457 B1 8/2001 Wallace et al.
6,287,301 B1 9/2001 Thompson et al.
6,319,228 B1 11/2001 Kastenhofer
6,344,041 B1 2/2002 Kupiecki et al.
6,397,850 B1 6/2002 Scheldrup et al.
6,423,085 B1 7/2002 Murayama et al.
6,428,489 B1 8/2002 Jacobsen et al.
6,440,088 B1 8/2002 Jacobsen et al.
6,450,987 B1 * 9/2002 Kramer ............. A61M 25/0023 604/523
6,468,266 B1 10/2002 Bashiri et al.
6,471,673 B1 10/2002 Kastenhofer
6,508,804 B2 1/2003 Sarge et al.
6,553,880 B2 4/2003 Jacobsen et al.
6,575,959 B1 6/2003 Sarge et al.
6,579,246 B2 6/2003 Jacobsen et al.
6,635,069 B1 10/2003 Teoh et al.
6,638,245 B2 10/2003 Miller et al.
6,648,874 B2 11/2003 Parisi et al.

(56) References Cited

U.S. PATENT DOCUMENTS

| | | | |
|---|---|---|---|
| 6,652,508 | B2 | 11/2003 | Griffin et al. |
| 6,656,550 | B1 | 12/2003 | Zamore |
| 6,702,782 | B2 | 3/2004 | Miller et al. |
| 6,702,802 | B1 | 3/2004 | Hancock et al. |
| 6,706,025 | B2 | 3/2004 | Engelson et al. |
| 6,733,459 | B1 | 5/2004 | Atsumi |
| 6,766,720 | B1 | 7/2004 | Jacobsen et al. |
| 6,780,181 | B2 | 8/2004 | Kroll et al. |
| 6,835,189 | B2 | 12/2004 | Musbach et al. |
| 6,849,062 | B2 | 2/2005 | Kantor |
| 6,860,893 | B2 | 3/2005 | Wallace et al. |
| 6,860,899 | B1 | 3/2005 | Rivelli |
| 6,878,151 | B2 | 4/2005 | Carrison et al. |
| 6,921,410 | B2 | 7/2005 | Porter |
| 6,936,055 | B1 | 8/2005 | Ken et al. |
| 6,997,937 | B2 | 2/2006 | Jacobsen et al. |
| 7,004,962 | B2 | 2/2006 | Stinson |
| 7,037,330 | B1 | 5/2006 | Rivelli et al. |
| 7,060,083 | B2 | 6/2006 | Gerberding |
| 7,070,607 | B2 | 7/2006 | Murayama et al. |
| 7,144,407 | B1 | 12/2006 | Lasersohn |
| 7,153,323 | B1 | 12/2006 | Teoh et al. |
| 7,166,122 | B2 | 1/2007 | Aganon et al. |
| 7,294,137 | B2 | 11/2007 | Rivelli et al. |
| 7,332,689 | B2 | 2/2008 | Mertens et al. |
| 7,412,285 | B2 | 8/2008 | Schroeppel et al. |
| 7,468,070 | B2 | 12/2008 | Henry et al. |
| 7,481,800 | B2 | 1/2009 | Jacques |
| 7,621,904 | B2 | 11/2009 | McFerran et al. |
| 7,645,259 | B2 | 1/2010 | Goldman |
| 7,654,979 | B2 | 2/2010 | Simpson |
| 7,742,811 | B2 | 6/2010 | Schroeppel et al. |
| 7,780,626 | B2 | 8/2010 | Wu et al. |
| 7,892,201 | B1 | 2/2011 | Laguna et al. |
| 7,942,847 | B2 | 5/2011 | Stupecky et al. |
| 7,998,165 | B2 | 8/2011 | Huffmaster |
| 8,066,667 | B2 | 11/2011 | Hayman et al. |
| 8,092,508 | B2 | 1/2012 | Leynov et al. |
| 8,202,292 | B2 | 6/2012 | Kellett |
| 8,206,373 | B2 | 6/2012 | Zhou |
| 8,348,890 | B2 | 1/2013 | Gerrans et al. |
| 8,961,550 | B2 | 2/2015 | Lenker et al. |
| 9,005,163 | B2 | 4/2015 | Bonnette et al. |
| 9,174,020 | B2 | 11/2015 | Allen et al. |
| 9,205,226 | B2 | 12/2015 | Allen et al. |
| 9,427,550 | B2 | 8/2016 | Dakin et al. |
| 9,550,046 | B1 | 1/2017 | Allen |
| 9,555,165 | B2 | 1/2017 | Phan |
| 9,844,383 | B2 | 12/2017 | Allen |
| 10,086,174 | B2 | 10/2018 | Crall et al. |
| 10,130,762 | B2 | 11/2018 | Allen |
| 10,350,382 | B1 | 7/2019 | Halstead et al. |
| 10,667,822 | B2 | 6/2020 | Allen |
| 10,780,252 | B2 | 9/2020 | Allen et al. |
| 10,786,660 | B2 | 9/2020 | Allen et al. |
| 11,123,482 | B2 | 9/2021 | Allen |
| 11,464,948 | B2 | 10/2022 | Halstead et al. |
| 2001/0008451 | A1 | 7/2001 | Ishii et al. |
| 2001/0041862 | A1 | 11/2001 | Glickman |
| 2002/0004666 | A1 | 1/2002 | Schwager et al. |
| 2002/0032457 | A1 | 3/2002 | Sirhan et al. |
| 2002/0193820 | A1 | 12/2002 | Wakuda et al. |
| 2003/0008726 | A1 | 1/2003 | Sano |
| 2003/0050600 | A1 | 3/2003 | Ressemann et al. |
| 2003/0114878 | A1 | 6/2003 | Diederich et al. |
| 2003/0125713 | A1 | 7/2003 | McGlinch et al. |
| 2003/0144657 | A1 | 7/2003 | Bowe et al. |
| 2003/0180488 | A1 | 9/2003 | Lim et al. |
| 2003/0191435 | A1 | 10/2003 | Shkolnik |
| 2003/0199914 | A1 | 10/2003 | Diaz |
| 2003/0220628 | A1 | 11/2003 | Kilsch et al. |
| 2004/0015151 | A1 | 1/2004 | Chambers |
| 2004/0073158 | A1 | 4/2004 | Shah et al. |
| 2004/0167415 | A1 | 8/2004 | Gelfand et al. |
| 2005/0131453 | A1 | 6/2005 | Parodi |
| 2005/0267407 | A1 | 12/2005 | Goldman |
| 2006/0106413 | A1 | 5/2006 | Bence et al. |
| 2006/0149186 | A1 | 7/2006 | Wantink et al. |
| 2006/0276886 | A1 | 12/2006 | George et al. |
| 2007/0055301 | A1 | 3/2007 | Campbell et al. |
| 2007/0088380 | A1 | 4/2007 | Hirszowicz et al. |
| 2007/0137651 | A1 | 6/2007 | Glassenberg et al. |
| 2007/0149927 | A1 | 6/2007 | Itou et al. |
| 2007/0197956 | A1 | 8/2007 | Le et al. |
| 2008/0033372 | A1 | 2/2008 | Briscoe et al. |
| 2008/0045908 | A1 | 2/2008 | Gould et al. |
| 2008/0208118 | A1 | 8/2008 | Goldman |
| 2008/0262470 | A1 | 10/2008 | Lee et al. |
| 2009/0131831 | A1 | 5/2009 | Wright et al. |
| 2009/0156999 | A1 | 6/2009 | Adams et al. |
| 2009/0177183 | A1 | 7/2009 | Pinkernell et al. |
| 2010/0030200 | A1 | 2/2010 | Strauss et al. |
| 2010/0113939 | A1 | 5/2010 | Mashimo et al. |
| 2010/0222637 | A1 | 9/2010 | Kassab |
| 2010/0249491 | A1 | 9/2010 | Faman et al. |
| 2011/0098671 | A1 | 4/2011 | Duffy et al. |
| 2012/0203173 | A1 | 8/2012 | Davies et al. |
| 2012/0253447 | A1 | 10/2012 | Hayasaka et al. |
| 2013/0116651 | A1 | 5/2013 | Takagi et al. |
| 2013/0131610 | A1 | 5/2013 | Dewaele et al. |
| 2013/0261545 | A1 | 10/2013 | Osypka |
| 2014/0163421 | A1 | 6/2014 | Van Hoven |
| 2014/0371718 | A1 | 12/2014 | Alvarez et al. |
| 2015/0112255 | A1 | 4/2015 | Jensen et al. |
| 2015/0351729 | A1 | 12/2015 | Chin et al. |
| 2016/0008585 | A1 | 1/2016 | Tano |
| 2016/0067444 | A1* | 3/2016 | Allen .................. A61M 25/005 604/524 |
| 2016/0096002 | A1 | 4/2016 | Di Caprio et al. |
| 2016/0101261 | A1 | 4/2016 | Kugler et al. |
| 2016/0199067 | A1 | 7/2016 | Smith et al. |
| 2016/0213893 | A1 | 7/2016 | Franklin |
| 2017/0049495 | A1 | 2/2017 | Yu et al. |
| 2017/0095646 | A1 | 4/2017 | Norman et al. |
| 2017/0113025 | A1 | 4/2017 | Chanduszko et al. |
| 2017/0252542 | A1 | 9/2017 | Iwano et al. |
| 2017/0303890 | A1 | 10/2017 | Yamashita |
| 2018/0015248 | A1 | 1/2018 | Logan et al. |
| 2018/0056036 | A1 | 3/2018 | Wada et al. |
| 2018/0071484 | A1 | 3/2018 | Raab et al. |
| 2020/0030577 | A1 | 1/2020 | Halstead et al. |
| 2020/0297351 | A1 | 9/2020 | Allen |
| 2022/0296864 | A1 | 9/2022 | Halstead et al. |

FOREIGN PATENT DOCUMENTS

| | | | |
|---|---|---|---|
| CN | 102802698 | A | 11/2012 |
| CN | 102805893 | A | 12/2012 |
| CN | 103298517 | A | 9/2013 |
| CN | 103764217 | A | 4/2014 |
| CN | 103987421 | A | 8/2014 |
| CN | 105228684 | A | 1/2016 |
| CN | 105246537 | A | 1/2016 |
| CN | 105854151 | A | 8/2016 |
| CN | 106422033 | A | 2/2017 |
| DE | 102009025347 | A1 | 12/2010 |
| DE | 202011003097 | U1 | 7/2011 |
| EP | 0520692 | A1 | 12/1992 |
| EP | 1121955 | A2 | 8/2001 |
| EP | 1131126 | B1 | 8/2004 |
| EP | 2389968 | A2 | 11/2011 |
| EP | 3132823 | A1 | 2/2017 |
| GB | 2512696 | A | 10/2014 |
| JP | H03-207376 | A | 9/1991 |
| JP | H05-015604 | A | 1/1993 |
| JP | H06-277296 | A | 10/1994 |
| JP | H07-213617 | A | 8/1995 |
| JP | H10244006 | A | 9/1998 |
| JP | 2003500121 | A | 1/2003 |
| JP | 2005511108 | A | 4/2005 |
| JP | 2006511271 | A | 4/2006 |
| JP | 2007319468 | A | 12/2007 |
| JP | 2008522716 | A | 7/2008 |
| JP | 2008544801 | A | 12/2008 |

(56) References Cited

FOREIGN PATENT DOCUMENTS

| | | | |
|---|---|---|---|
| JP | 2011087971 | A | 5/2011 |
| JP | 2011152181 | A | 8/2011 |
| JP | 201290779 | A | 5/2012 |
| JP | 2015523884 | A | 8/2015 |
| JP | 2016517778 | A | 6/2016 |
| KR | 20100006710 | U | 7/2010 |
| WO | WO89/08471 | A1 | 9/1989 |
| WO | WO99/48548 | A1 | 9/1999 |
| WO | WO00/32264 | A1 | 6/2000 |
| WO | WO2004/107965 | A2 | 12/2004 |
| WO | WO2007/121005 | A1 | 10/2007 |
| WO | WO2012/009486 | A2 | 1/2012 |
| WO | WO2012/099979 | A1 | 7/2012 |
| WO | WO2014/008489 | A1 | 1/2014 |
| WO | WO2017/142941 | A1 | 8/2017 |
| WO | WO2019/236951 | A1 | 12/2019 |
| WO | WO2020/023889 | A1 | 1/2020 |
| WO | WO2021/035042 | A1 | 2/2021 |
| WO | WO2023/278594 | A1 | 1/2023 |

OTHER PUBLICATIONS

BMI ESPICOM Pharmaceutical and Medical Device News; Business Monitor Online: Vascular solutions expands complex intervention offerings with turnpike LP catheter; newsleter; 2pages; retrieved from the internet (https://dialog.proquest.com/professional/docview/1753127273?accountid=157282) on Apr. 18, 2018 (Abstract Only).

Cliffton et al.; Technique for visualization and perfusion of bronchial arteries: suggested clinical and diagnostic applications; Cancer; 16; pp. 444-452; Apr. 1963.

Cook Medical; Flexor technology; 16 pages; retrieved from the internet (https:cookmedical.com/data/resources/PI-BM-KCF-EN-201302_WEB.pdf) on May 5, 2019.

Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.

Nordson Medical; Extruded tubing technical information; 7 pages; retrieved from the intemet (https://www.nordsonmedical.com/Components-and-Technologies/Medical-Tubing/Extruded-Tubing/Technical-Information/) on Aug. 17, 2018.

Rousselot et al.; Selective concentration of anticancer drugs in the liver: Hepatic-artery infusion and induced hepatic outflow block; JAMA; 191(9); pp. 707-710; Mar. 1965.

Vante Plasticweld Systems; Bonds and welds; 13 pages; retrieved from the internet (https://cathetertipping.com/home/our-products/bonding/) on Aug. 17, 2018.

Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).

Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.

Halstead et al.; U.S. Appl. No. 17/938,559 entitled "Balloon catheters and methods of manufacture and use," filed Oct. 6, 2022.

* cited by examiner

CATHETERS ADAPTED FOR AGENT DELIVERY

CROSS REFERENCE TO RELATED APPLICATIONS

This patent application is a 371 of International Application No. PCT/US2022/035545, filed Jun. 29, 2022, which claims the benefit of U.S. Provisional Patent Application No. 63/202,989, filed Jul. 2, 2021, the entire disclosures of which are fully incorporated by reference herein for all purposes.

This application also incorporates the entire disclosures of the following patents and applications by reference herein for all purposes: U.S. Pat. No. 9,550,046; U.S. 2020/0023170; U.S. U.S. Pat. No. 10,350,382; and U.S. 2020/0030577.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Catheters may be adapted to deliver agents (e.g., fluid agents, therapeutic agents, contrast agents, etc.) into patients, examples of which are described in U.S. Pat. No. 9,550,046; U.S. 2020/0023170; U.S. Pat. No. 10,350,382; and U.S. 2020/0030577, which are incorporated by reference herein for all purposes. When the catheters are relatively small (e.g., microcatheters), particles in the agent(s) being delivered through a lumen may tend to stick or clump together when delivered through a relatively small lumen, which can block the lumen. Additionally, some small lumen microcatheters cannot allow passage of some relatively larger particles, which can prevent the catheter from being used for the procedure. Additionally, a contrast agent may be injected under pressure through a microcatheter lumen for imaging the vasculature. In small lumen catheters, contrast may not flow fast enough to achieve a clear picture. There is a need for catheters, particularly microcatheters, that address one or more of these challenges.

SUMMARY

The application is related to elongate medical devices (e.g., catheters), their methods of use, and manufacture.

It is understood that any feature in any of the aspects, examples, or embodiments of this application (including figures), including in any materials incorporated by reference herein, may be combined with any other suitably combinable feature herein, even if not explicitly described as being combined or combinable in any particular aspect, example, or embodiment.

One aspect of the disclosure is a catheter for delivering an agent into a patient, where the catheter may include any of the features shown or described herein.

In this aspect, the catheter may include one or more deformable lumens. The one or more deformable lumens may have a collapsed configuration and an open configuration. The change in configuration generally creates a larger space or area within the catheter for an agent to be delivered, thereby addressing one or more of the challenges mentioned herein.

In this aspect, the catheter may optionally include an outer shaft, which optionally may comprise one or more agent delivery ports.

In this aspect, the catheter may optionally include a guidewire channel, the guidewire channel defining a guidewire lumen sized and configured to receive a guidewire therein.

In this aspect, the catheter may include an inflatable balloon, optionally carried by a distal region of the catheter.

In this aspect, the catheter may optionally include a balloon inflation channel within the outer shaft, the balloon inflation channel defining a balloon inflation lumen in fluid communication with an internal volume of an inflatable balloon.

In this aspect, the catheter may optionally include an agent delivery lumen. An agent delivery lumen may optionally be defined by one or more surfaces of the catheter, such as an inner surface of an outer shaft, an outer surface of a guidewire channel and an outer surface of a balloon inflation channel. Any agent delivery lumen may be communication with the one or more agent delivery ports, the one or more agent delivery ports optionally proximal to at least a portion of an inflatable balloon.

In this aspect, a proximal portion of a guidewire channel may be deformable between an open configuration and a collapsed configuration.

In this aspect, a proximal portion of a guidewire channel may be biased to a collapsed configuration.

In this aspect, a proximal portion of a guidewire channel may optionally be adapted to deform towards a collapsed, agent-delivery configuration in response to an increase in fluid pressure in an agent delivery lumen.

In this aspect, an open configuration of a channel may optionally be a circular cross-sectional configuration, and a collapsed configuration of a channel may not be a circular cross-sectional configuration.

In this aspect, a lumen (e.g., a guidewire lumen), in a cross-section transverse to a long axis of the catheter and through a proximal portion of the channel, optionally has an area when the channel is in an open configuration that is greater than an area when the channel is in a collapsed configuration.

In this aspect, an agent delivery lumen, in a cross-section transverse to a long axis of the catheter and through a proximal portion of a channel, optionally has an area when the channel is in an open configuration that is less than an area when the channel is in a collapsed configuration.

In this aspect, in a proximal portion of a channel, an agent delivery lumen optionally has a greater volume when the channel is in a collapsed configuration than when the channel is in an open configuration.

In this aspect, a channel (e.g., guidewire channel) is optionally not adapted to collapse in a distal portion, the distal portion optionally extends within an inflatable balloon.

In this aspect, the catheter may optionally include a balloon support adapted to support an inflatable balloon. A balloon support may optionally be coupled to a balloon inflation channel. A balloon support may optionally comprise one or more balloon inflation ports in fluid communication with a balloon inflation lumen and an internal volume of the inflatable balloon to facilitate inflation of the inflatable balloon.

In this aspect, an inflation channel may optionally have a distal end that is disposed within a first lumen defined by a balloon support, the first lumen optionally in fluid communication with one or more balloon inflation ports.

In this aspect, the catheter may optionally include a balloon support that comprises a first lumen, wherein the first lumen may optionally have a non-circular cross-sectional configuration.

In this aspect, the catheter may optionally include a balloon inflation channel that has a first circular cross-sectional configuration in a first portion that is proximal to a balloon, and a second non-circular cross-sectional configuration in a second portion within a first lumen of a balloon support.

In this aspect, the catheter may optionally include a balloon support with a support lumen therein, and wherein at least a portion of a channel (e.g., a guidewire channel) may optionally be disposed within the support lumen. A channel may extend through a support lumen and optionally at least to a distal end of a support lumen.

In this aspect, an outer shaft of a catheter may optionally be secured to a proximal end of a balloon support, and wherein a balloon may be secured (which includes directly or indirectly secured) to a balloon support.

In this aspect, an optional balloon support may be adapted to prevent elongation thereof to thereby prevent elongation of a balloon that supported by the balloon support.

In this aspect, an optional balloon support may optionally comprise one or more strengthening elements adapted and positioned to prevent elongation of a balloon that is supported by the balloon support.

In this aspect, the catheter may optionally include a balloon support, wherein a distal portion of a guidewire channel may be secured to the balloon support such that the distal portion of the guidewire channel is not collapsible.

In this aspect, a proximal portion of a channel (e.g., a guidewire channel, or an agent delivery channel) may be is biased to an open configuration.

In this aspect, the catheter may include one or more agent delivery ports, which may be proximal or distal (and optionally both) to a balloon.

In this aspect, the catheter may include an agent delivery lumen that has, in a cross-section transverse to a long axis of the catheter, a configuration that is changeable from a first configuration to a second configuration (changeable without changing a configuration of an outer surface of the catheter). The agent delivery lumen may have, in the cross section, an area that is greater in the second configuration than in the first configuration. The agent delivery lumen may optionally be biased to a second, open, configuration, where the bias may exist due to collapse of a channel within the catheter (e.g., a guidewire channel).

In this aspect, the catheter may include an inflatable balloon and one or more agent delivery ports in an outer shaft, wherein the agent delivery ports may be proximal to at least a portion of the balloon.

In this aspect, the catheter may include a channel within the catheter (e.g., a guidewire channel) where a proximal portion of the channel may be deformable between an open configuration and a collapse configuration but a distal portion of the channel may not be deformable. A distal, non-collapsible portion may extend axially within an inflatable balloon.

In this aspect, the catheter may optionally include an inflatable balloon, an outer shaft, and an inner shaft that is co-axial with the outer shaft, the inner shaft extending distally beyond a distal end of the outer shaft, the outer shaft and the inner shaft defining therebetween a balloon inflation lumen that is in communication with the inflatable balloon, and wherein the inner shaft is deformable between an open configuration and a collapsed configuration. In this example, the inner shaft may be a guidewire channel and/or an agent delivery channel. The balloon inflation lumen (between the shafts) may be larger when the inner shaft assumes the collapsed configuration, such as in FIG. 6B. The guidewire lumen may be smaller when the inner shaft assumes the collapsed configuration, such as in FIG. 6B.

Any of the cross-sectional areas or volumes of lumens that are described herein may be at least one and a half times as large when a channel or lumen is an open configuration compared to a collapsed configuration (i.e., 150% of the area or volume of the collapsed configuration). For example, the area of the guidewire lumen in the cross section in FIG. 1A may be at least one and a half times as large as the area of the guidewire lumen in the collapsed configuration shown in FIG. 1B. Additionally, for example, the area of the agent delivery lumen in FIG. 1B (which may be considered an open configuration of the agent delivery lumen) may be one and a half times as large as the area of the agent delivery lumen in FIG. 1A (FIG. 1A may be considered a collapsed configuration of the agent delivery lumen as a result of the guidewire lumen having an open configuration).

Any of the components of any of the catheters herein may have dimensions and/or other features that are described in any of the references incorporated by reference, such as the thicknesses of shafts, balloon materials, channels or lumen dimensions, etc.

DETAILED DESCRIPTION

Figure 1A:
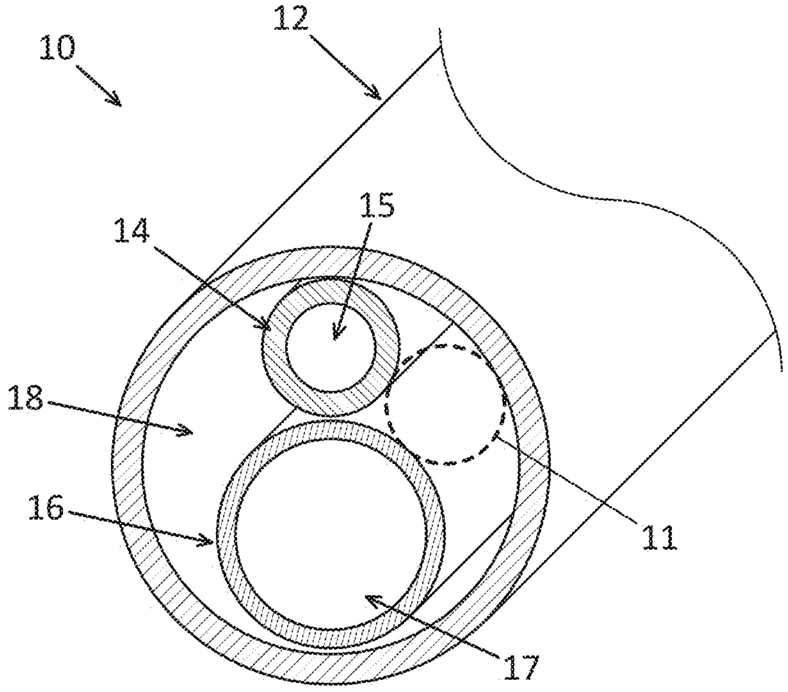
FIGS. 1A and 1B illustrate a portion of an exemplary catheter with at least one deformable lumen.

One aspect of this disclosure is related to catheters, optionally microcatheters, that include at least one deformable lumen. Some catheters and procedures may benefit from having one or more lumens therein that are deformable. While the disclosure herein may describe exemplary catheters with one or more collapsible lumens, it is understood that the concepts herein may be applicable to other types of catheters. For example, catheters described in U.S. Pat. No. 9,550,046; US 2020/0023170; U.S. Pat. No. 10,350,382; and US 2020/0030577 (all of which are incorporated by reference herein) may incorporate a deformable guidewire lumen, such as those that are described herein.

The lumens herein are generally spaces or volumes that may be defined by one or more surfaces or structures of the catheter. When the disclosure refers to deformable lumens, it is understood that it is referring to the one or more deformable surfaces or structures that define the deformable lumen.

The catheters herein may be adapted to deliver one or more agents (e.g., therapeutic agents, contrast agents, etc.) into a patient, such as into a blood vessel in a patient, examples of which are describe in U.S. Pat. No. 9,550,046; US 2020/0023170; U.S. Pat. No. 10,350,382; and US 2020/0030577. Catheters herein may optionally include an inflatable balloon structure that is adapted to be inflated to occlude a vessel in which the catheter is placed and/or help stabilize the catheter in the vessel. In some examples herein, an agent delivery port is located distal relative to the balloon such that the agent is delivered into the patient distal to the inflated balloon.

For some applications, however, it may be advantageous to deliver an agent (e.g., a drug) at a location of the catheter that is proximal to an inflated balloon. In these examples, the one or more drug delivery ports are disposed proximal to the balloon, and in examples herein this may be implemented by having the one or more drug delivery ports in an outer wall of an outer elongate shaft of the catheter.

In some implementations, the catheters may be dimensioned such that spaces between surfaces (e.g., walls) are relatively small, and in some instances the catheters may be considered microcatheters. When delivering some therapeutic agents that include particles through a lumen in the catheter, the size of the particles and lumen size(s) may tend to cause the particles to stick and clump to each other. Particles clumping (i.e. sticking together) can block a small lumen. Small lumen microcatheters cannot allow passage of relatively larger particles and cannot be used for the procedure. By way of example, uterine fibroid embolization requires particles that are between 500 microns and 900 microns. This size may not advance through a microcatheter with a small lumen. Additionally, a contrast agent is also typically injected under pressure through the microcatheter lumen to image the arteries distal to the catheter tip. In small lumen catheters, contrast may not flow fast enough to achieve a clear picture.

In this regard, it may be advantageous for the catheters herein to include an agent delivery lumen that has as much open space, volume, or area in cross section as possible to, for example, prevent or at least reduce the likelihood of agent particles sticking to each other when the fluid agent is delivered through the agent delivery channel of the catheter, as well as optionally allowing a contrast agent to be delivered at a high enough flow rate to achieve a clear image. In some of the embodiments herein, an agent delivery lumen may be at least partially defined by one or more internal surfaces or channels that are disposed within an outer shaft of the catheter, such as a guidewire channel disposed within an outer shaft of a catheter. In some examples herein, a guidewire channel is adapted to deform so as to increase an internal space or volume of an agent delivery channel through which the agent is delivered, so as to prevent or reduce the likelihood of particulate in the agent from sticking and clumping to each other. While some examples below illustrate a guidewire channel that is deformable and the drug delivery port is proximal to the balloon, additional examples below describe catheters with a deformable guidewire channel that is also an agent delivery channel, and wherein the agent delivery port is distal to the balloon.

It is understood that any particular feature or features of any particular example or embodiment herein may be combined with any other suitably combinable feature or features of any other example or embodiment herein.

Figure 1B:
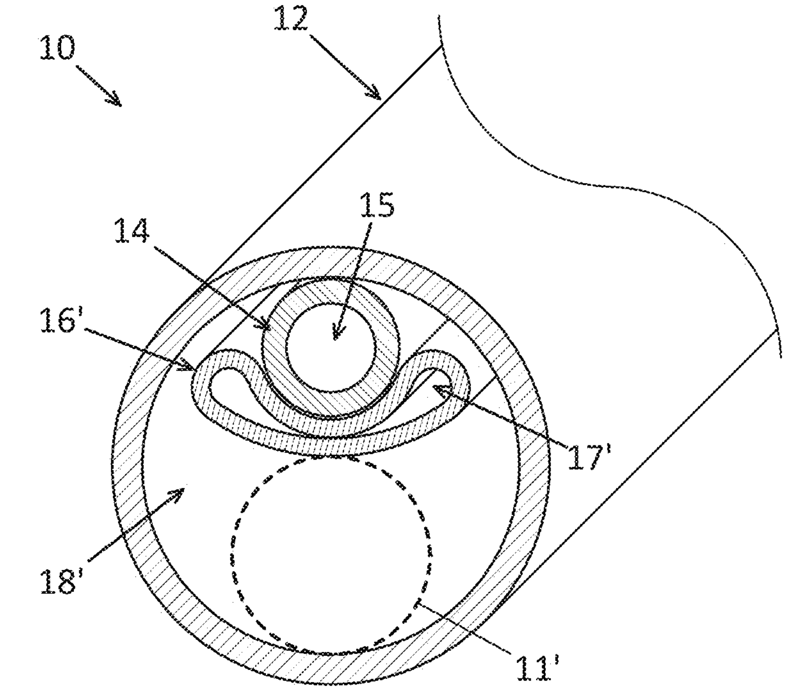

FIGS. 1A and 1B illustrate partial sectional perspective views of a portion of exemplary catheter 10 in a section (transverse to a long axis of the catheter) proximal to an inflatable balloon (not shown). FIG. 1A illustrates catheter 10 when channel 16 (e.g., a guidewire channel) is in an open, or non-collapsed, configuration or state, and FIG. 1B illustrates catheter 10 when channel 16' is in collapsed configuration or state, as shown. Catheter 10 also includes an agent delivery channel that defines an agent delivery lumen 18, wherein in this example the agent delivery channel is defined by an inner surface of outer shaft 12 and outer surfaces of inflation channel 14 and guidewire channel 16. As described below, either of guidewire channel 16 or 16' may be considered a deformed configuration, with the other configuration being considered an at-rest or neutral configuration. That is, the guidewire channel may be adapted such that it is biased to revert or return naturally to either the open or the collapsed configuration, and in both cases the guidewire channel (and the guidewire lumen) is considered deformable. In this example, the agent delivery channel and the agent delivery lumen 18 and 18' have a plurality of configurations, which in this example depends on the deformability of the guidewire channel 16. That is, the agent delivery lumen 18/18' is also considered deformable between an open configuration (FIG. 1B) and a collapsed configuration (FIG. 1A).

The examples herein may describe a channel as a guidewire channel or an inflation channel, but it is understood that in alternative designs, the catheters herein may include a deformable channel that is not used as a guidewire channel or as a inflation channel.

As shown in the sectional view of FIG. 1B, the agent delivery lumen 18' in this cross section has a greater area than the area of agent delivery lumen 18 shown in FIG. 1A. The volume of agent delivery lumen 18' is also greater than the volume of agent delivery lumen 18 in the portion (or region) of the catheter proximal to the optional balloon. In this example, the guidewire channel is adapted to deform to essentially create a larger and more uninterrupted space within the catheter for agent delivery so as to prevent or reduce the amount of particle sticking or clumping compared to delivery of the same agent (e.g., a therapeutic) when the guidewire channel is not deformed (e.g., as in FIG. 1A). An alternative way of characterizing the difference in configuration of the agent delivery lumen shown between FIGS. 1A and 1B is that the largest inscribed circle (shown in dotted lines 11 and 11' respectively) between internal surfaces in FIG. 1B has a larger diameter than the largest inscribed circle between internal surfaces in FIG. 1A, as shown. FIGS. 1A and 1B illustrate an example of a catheter that is adapted such that an agent delivery channel and an agent delivery lumen have different configurations in the same cross section, and in this example, this is due to the deformability of a channel within the catheter, which in this particular implementation is a guidewire channel.

In this example and in the sections shown in FIGS. 1A and 1B, the internal area of the guidewire lumen 17' when in the collapsed configuration (FIG. 1B) is smaller than the area of the guidewire lumen 17 when in the open configuration (FIG. 1A). In this example and in the sections shown in FIGS. 1A and 1B, the internal area of the agent delivery lumen 18' when in the open configuration (FIG. 1B) is larger than the area of the agent delivery lumen 18 when in the collapsed configuration (FIG. 1A). The advantages herein can be realized when delivering an agent through the agent delivery lumen when the lumen 18' is in the configuration shown in FIG. 1B.

Internal catheter lumens and channels herein that are described as being deformable or having multiple configurations are adapted to be deformable or have multiple configurations when an outer catheter surface is not deformed. This description is meant to distinguish deformable channels or lumens that may be deformed in response to an external force or pressure exerted on an outer surface of the catheter (e.g., an outer shaft 12). That is, the channels and lumens herein can be deformed or have their configurations changed when the outer shaft of the catheter is not deformed, which is shown in the comparison in exemplary FIGS. 1A and 1B, in which the shaft 12 has the same configuration in both figures.

Figure 1C:
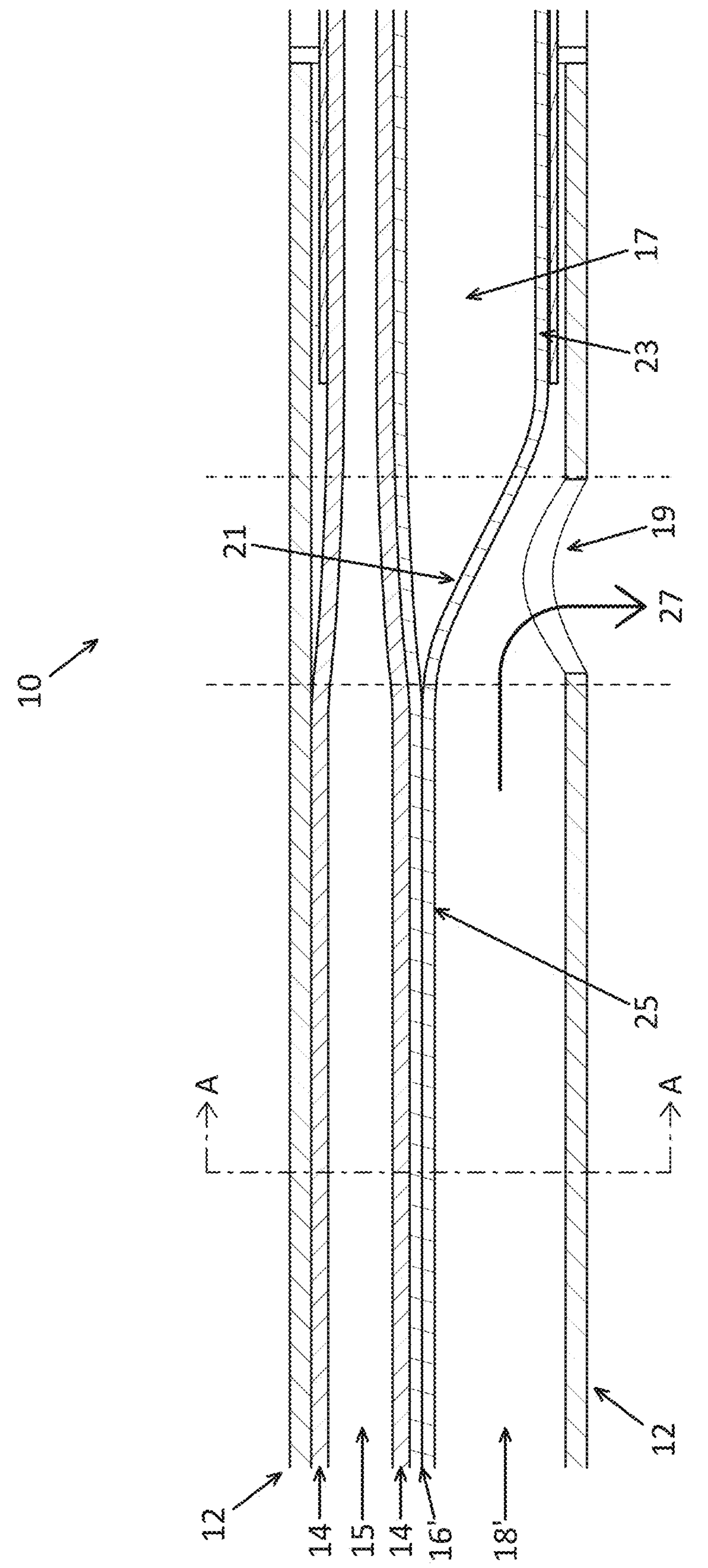
FIG. 1C is a side view of a portion of an exemplary catheter with at least one deformable lumen.

FIG. 1C illustrates a side partial sectional view of catheter 10, showing half of a portion of the catheter (the optional balloon is not shown). Catheter 10 includes at least one agent port 19 in outer shaft 12 out of which an agent (e.g., drug) may be delivered. FIG. 1C illustrates a proximal portion of guidewire channel 16' in the deformed configuration that is shown in FIG. 1B. In this example, guidewire channel 16' is adapted to deform in region or portion 25, such as in response to removal of a guidewire from the guidewire lumen and/or an increase in fluid pressure in agent delivery lumen 18'. Guidewire channel 16' also includes region or portion 23, which in this embodiment is distal to drug port 19 and distal to region 25, that is not adapted to deform. Region 23 of guidewire channel 16' includes a region of the guidewire channel that extends within the inflatable balloon, described in more detail elsewhere herein. Guidewire channel 16' includes a transition region or portion 21 that is between the deformed region or portion 25 and region or portion 23 that is not adapted to deform (and is not deformed). When portion 25 is collapsed, transition portion 21 is a portion of the guidewire channel where the configuration of the channel transitions (in a proximal to distal direction) from the configuration shown in FIG. 1B to a different configuration, such as the circular configuration shown in FIG. 1A. Transition portion 21 may also be considered a portion of the channel where the guidewire channel transitions from a first collapsed configuration to a non-deformed or non-collapsed configuration. Transition portion 21 may also be considered a portion of the channel where the guidewire channel transitions from a first configuration to a second configuration that is different than the first configuration. In this example, at least a region of transition portion 21 axially overlaps with agent port 19 (along the length of the port 19), as is illustrated with the vertical dashed lines in FIG. 1C. In alternative designs, however, a transition region may be disposed entirely distal to the one or more agent ports 19 (but may optionally still be proximal to an optional balloon). The transition region may be axially overlapping with or distal to the agent port 19 to create sufficient space for the agent 27 that is delivered through agent delivery lumen 18' to exit out of agent port 19, which is illustrated by arrow 27 in FIG. 1C.

In some embodiments, the deformable channel (e.g., a guidewire channel) is a single monolithic structure with the same material (e.g., polymeric) throughout. The material of the guidewire channel in regions 23 and 25 may therefore be the same, but it may be adapted to deform in region 25 but not in region 23 due to factors other than the material of the guidewire channel. For example only, region 23 may be adapted such that it is adapted not to deform because the guidewire channel is coupled to one or more components of catheter 10, wherein the coupling prevents the distal portion from deforming, an example of which is shown and described in more detail with respect to FIGS. 2A and 2B. For example, the guidewire channel may not be collapsible or deformable within balloon support 30, described below in reference to FIGS. 2A-2E, and it can be adhered to at least a proximal end or proximal end region of balloon support 30 to prevent the channel from collapsing within balloon support 30. Alternatively, or additionally, an increase in fluid pressure may occur primarily proximal to and at the location of agent port 19, such that the fluid pressure within the agent delivery lumen does not increase sufficiently in a region that is distal to agent port 19, and therefore there may be minimal or no deformation of the guidewire channel distal to the drug port.

Figure 2A:
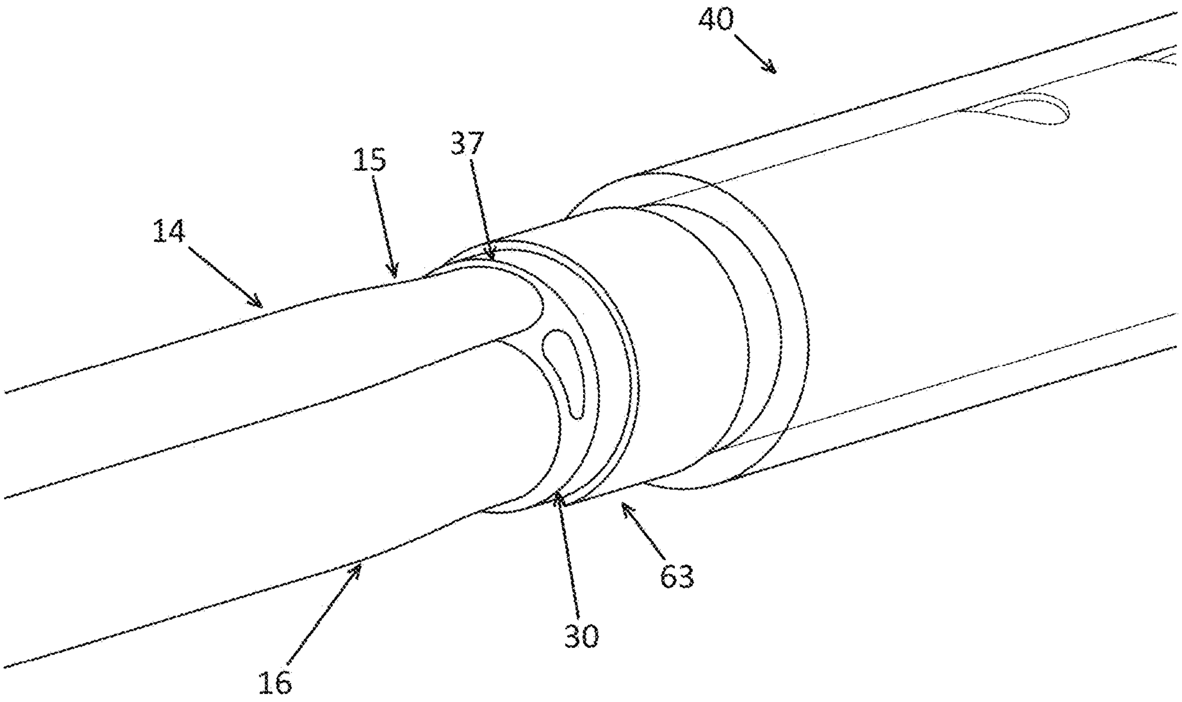
FIGS. 2A and 2B illustrate optional and exemplary coupling between channels and a balloon support.
Figure 2B:
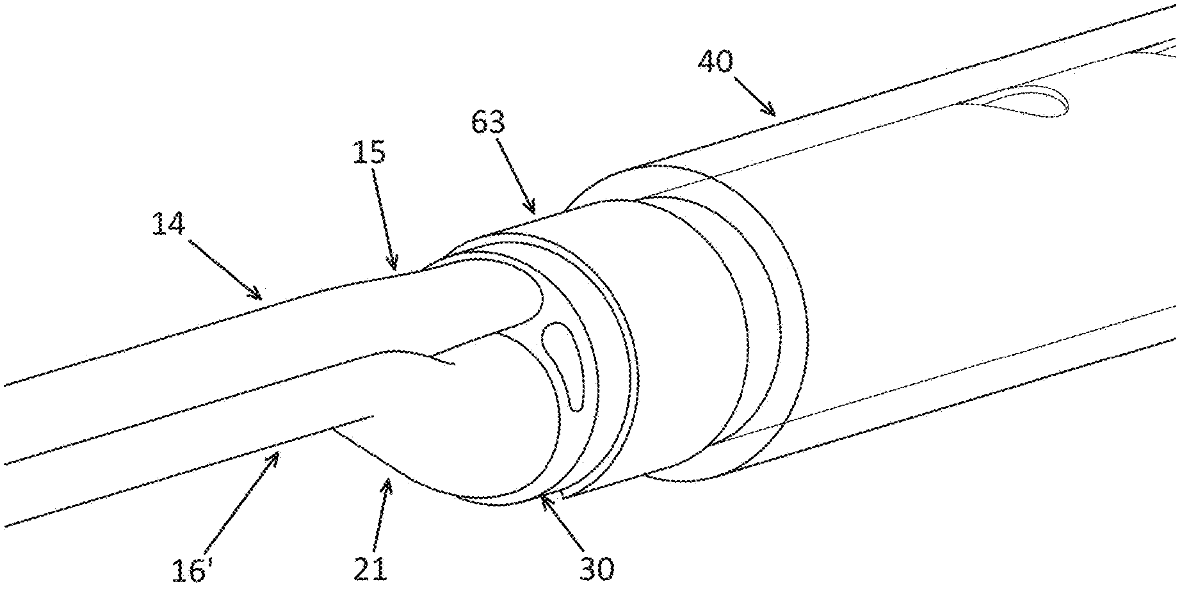
Figure 2C:
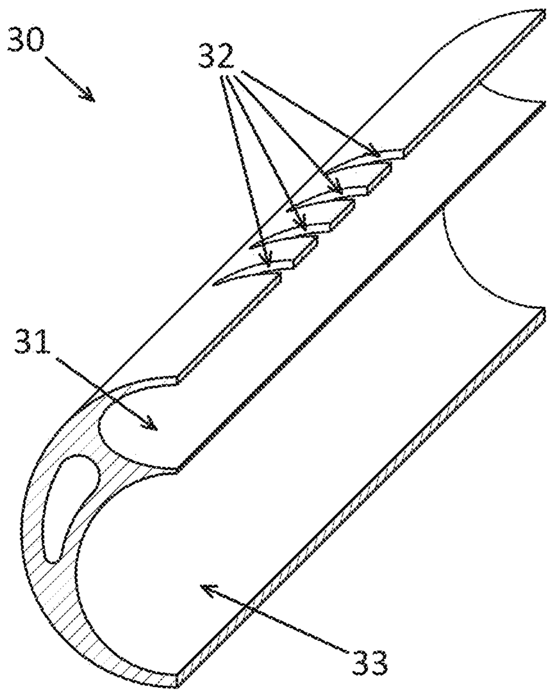
FIGS. 2C, 2D and 2E illustrate an optional and exemplary balloon support.
Figure 2D:
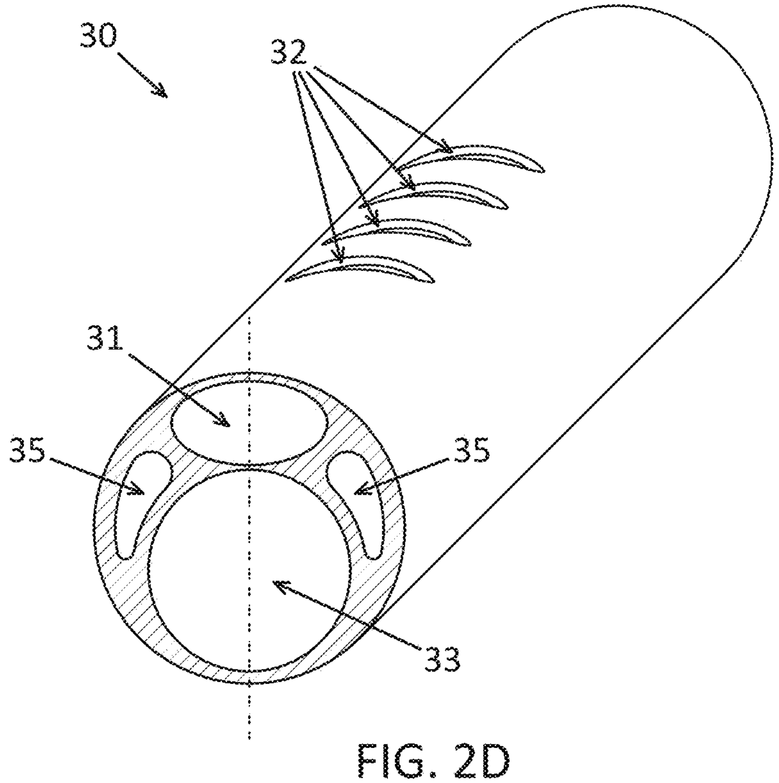
Figure 2E:
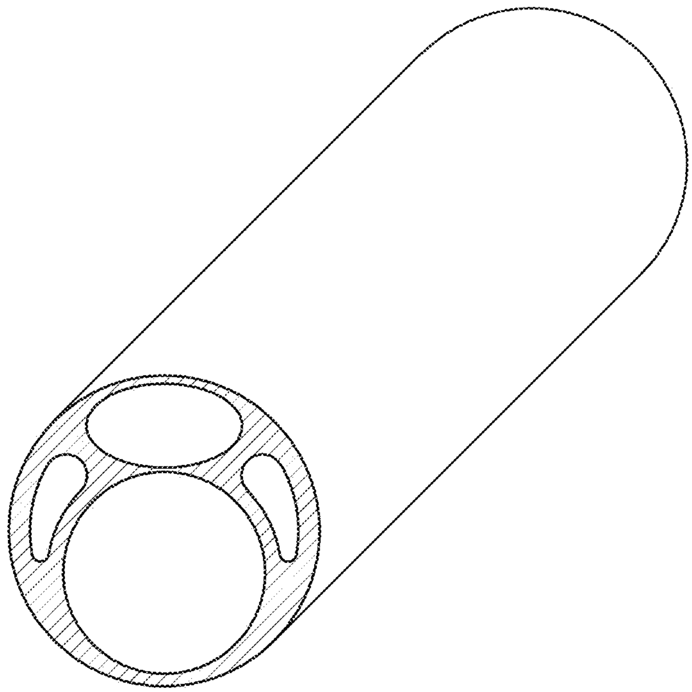

Exemplary catheter 10 also includes an optional balloon support, a mere example of which is shown in FIGS. 2A-2E, wherein the balloon support is sized and configured, generally, to support the optional balloon (either direct or indirect coupling). In this example, balloon support 30 defines and includes first lumen 31 and second lumen 33, which in this example are balloon inflation lumens 31 and guidewire channel lumens 33, respectively. As shown in FIG. 2A, a distal region of inflation channel 14 is disposed within first lumen 31, which creates fluid communication between inflation channel 14 and inflation lumen 31. Balloon support 30 also includes one or more balloon inflation ports 32 (or inflation ports) that are in fluid communication with first lumen 31, such that a balloon inflation fluid may be delivered through inflation channel 14, into inflation lumen 31 and out of balloon inflation ports 32 to cause balloon 40 to expand to an inflated and expanded configuration (e.g., such as shown in FIG. 2H). Inflation channel 14 may alternatively extend through inflation lumen 31 in support 30 and distal to the inflation ports 32 (and optionally beyond), in which case inflation channel 14 would also include one or more inflation ports therethrough to facilitate the fluid communication from within the inflation channel 14 to balloon inflation ports 32 in balloon support 30.

In this example, guidewire channel 16 extends into and through second or guidewire channel lumen 33, as is shown in FIGS. 2A, 2B, 2F, 2G and 2H.

Figure 2F:
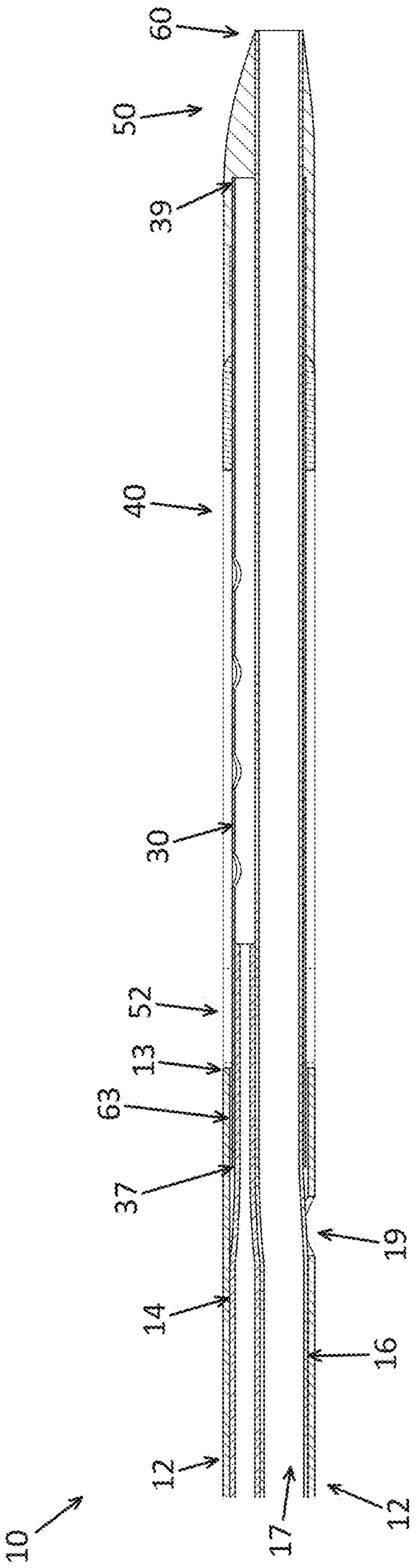
FIGS. 2F and 2G illustrate side views of a portion of an exemplary catheter with at least one deformable lumen.
Figure 2G:
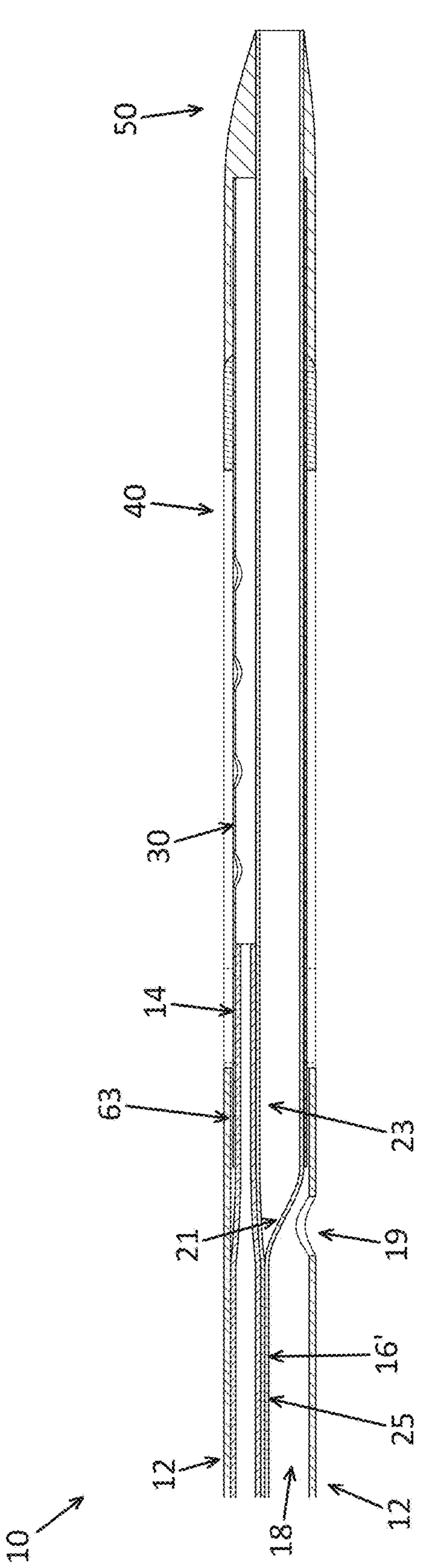
Figure 2H:
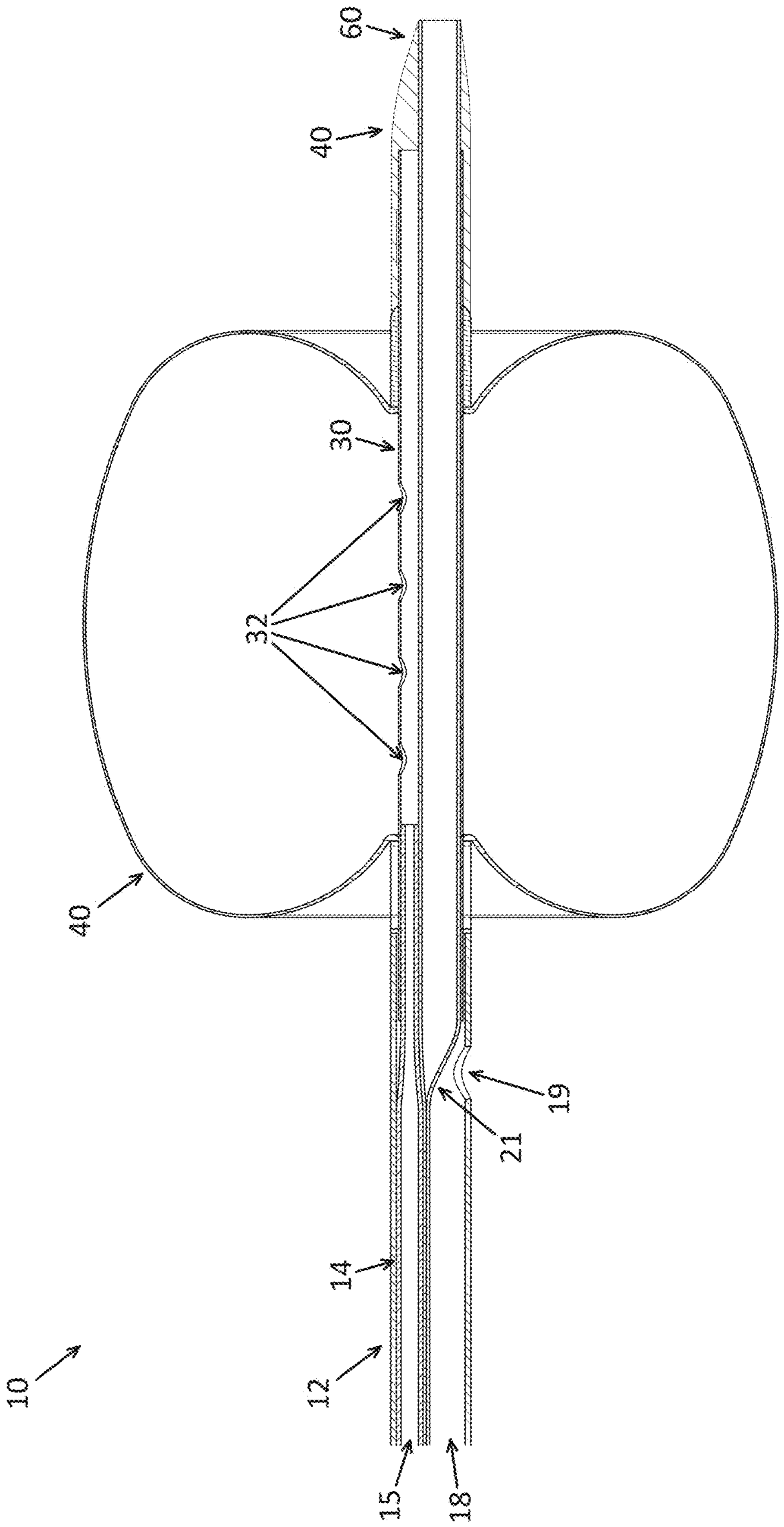
FIG. 2H illustrates an inflatable balloon in an expanded configuration.
Figure 2I:
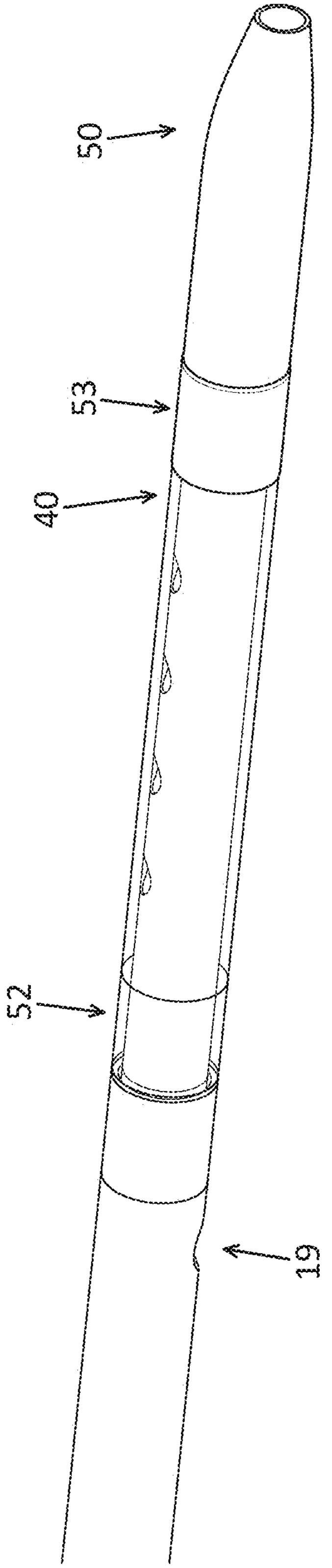
FIGS. 2I and 2J are perspective and side views, respectively, of an exemplary catheter with a balloon that is in a non-expanded configuration.

FIGS. 2F and 2G illustrate a side sectional view of the distal region of catheter 10 (showing half of a portion of the catheter), including a distal end 60 thereof. FIG. 2F illustrates guidewire channel 16 and guidewire lumen 17 in first, open, configurations, and FIG. 2G (a portion of which is shown in FIG. 1C) illustrates guidewire channel 16' with portion 25 in a second, collapsed, configuration, which is also shown in FIGS. 1B, 1C and 2B, which provides the benefits described herein.

In some uses, a guidewire (not shown, but which is understood in the art) may be disposed within guidewire channel 16, such as in the configuration shown in FIG. 2F. For example, a guidewire may be advanced towards a target location within a patient and the catheter may be advanced over the guidewire with the guidewire in the guidewire lumen. Alternatively, the catheter may be delivered first, and a guidewire may be incrementally advanced distally with the catheter advanced distally to follow the guidewire. Methods of use herein may include a variety of methods of delivery and positioning that involve the use of a guidewire within a guidewire lumen.

In some examples, portion 25 of guidewire channel 16 may be adapted to automatically or naturally revert towards a collapsed configuration when a guidewire is removed proximally from guidewire channel 16. For example, a guidewire (not shown) may be disposed within and extend within guidewire channel 16 in the configuration shown in FIG. 2F. In some examples, when a guidewire is retracted proximally and removed from guidewire channel 16, region 25 of guidewire channel 16' may be adapted and configured (biased) to revert or deform towards the collapsed configuration, such as is shown in FIG. 2G (and FIGS. 1B, 1C and 2B). When the guidewire is initially introduced into guidewire lumen 17, the guidewire channel 16 may be adapted to deform and expand easily to accommodate the presence of the guidewire as the guidewire is advanced distally therein.

Additionally, in this example, region 23 of the guidewire channel is not adapted and configured to revert to or towards a different configuration (in this example a collapsed configuration). Portion or region 23 of the guidewire channel extends distally through the balloon and to catheter tip 50, as well as distal end 60 of the catheter. Region 23 does not need to be collapsible in this example because agent port(s) 19 is proximal to the balloon, and thus there is not a benefit to opening the agent delivery pathway distal to agent port 19.

In some examples, guidewire channel 16 may be formed (e.g., extruded) in the collapsed/deformed configuration (e.g., FIG. 1B, 1C, 2B), such that when a guidewire is removed therefrom the guidewire channel will naturally or automatically revert towards the collapsed state/configuration. In these examples the guidewire lumen is biased towards the deformed/collapsed configuration. In some examples, the guidewire channel may be formed in the open (non-collapsed) configuration, after which it may be collapsed and set in the collapsed state, such that when the guidewire is removed the channel will automatically revert to (be biased towards) the collapsed state.

In some examples, the guidewire channel may be biased towards a collapsed configuration, but an increase in pressure in the agent lumen may more fully collapse the guidewire channel to the collapsed configuration. In these examples, the guidewire channel may be biased to partially collapse, and may also be adapted to more fully collapse in response to an increase in fluid pressure in the agent delivery lumen.

In some examples, region 25 of guidewire channel 16 is not adapted to automatically transition or revert to a collapsed configuration upon withdrawal of a guidewire. For example, delivery of a fluid into agent delivery lumen 18 may increase the fluid pressure within agent lumen 18, which may cause the guidewire channel portion 25 to transition or deform towards the collapsed configuration. At least portion 25 may be made of material(s) (e.g., one or more polymeric materials) such that an increase in pressure in lumen 18 causes the configuration of portion 25 to change or deform.

In any of the embodiments herein, the guidewire channel may be a flexible and preferably has some lubricity at least internally to accept a guidewire therein. In some examples herein the guidewire channels may be PTFE, for example only.

The catheters herein may include a balloon support. Exemplary balloon support 30 has a cylindrical outer profile, and may optionally be formed by an extrusion process (e.g., may include one or more polymeric materials). Balloon support 30 is generally flexible, but is adapted to avoid elongation, which helps control the inflated shape of the balloon when inflated. If support 30 were adapted to elongate, or stretch axially, this could cause the balloon to assume an inflated configuration other than an intended or desired inflated configuration. Balloon support 30 may include or house therein one or more additional parts or components to strengthen support 30 and prevent elongation or stretching thereof. For example only, support 30 may include one or more strengthening element cavities 35, in which, in some examples, may be disposed fibers that are adapted not to stretch, which can thereby prevents balloon support 30 from elongating or stretching axially. In some examples, strengthening elements may include one more of Kevlar® fibers, which may optionally be disposed in one or more cavities 35 in the balloon support, examples of which are shown in FIG. 2D.

Inflation lumen 31 may have a distal end that is blocked or sealed. This may be due to inflation lumen being formed with a closed distal end, or optionally the distal end of lumen 31 may be blocked off with a different component, such as with a surface of tip 50, as shown in FIGS. 2F and 2G. Tip 50 in this example is disposed over a distal region of balloon support 30 and acts as a stop for the inflation fluid, which allows the inflation fluid to exit balloon inflation ports 32 and inflate balloon 40, as shown in FIG. 2H. In any of the embodiments herein, inflation lumen 31 may have a filling material in its distal end to help seal the distal end off, in which case the filling material would be disposed only distal to the distal most balloon inflation port 32 (or distal to the only port 32 if there is only one inflation port 32).

In some examples, inflation lumen 31 of balloon support 30 may not have a circular cross-sectional configuration, such as in the example shown in FIG. 2A-2E (e.g., oval). In some examples, the guidewire channel may need to be a certain size and circular/round to accommodate a guidewire, which in these examples takes up a fairly large volume of balloon support. This may limit the dimension of inflation lumen 31 in the direction along the hashed line in FIG. 2D. To increase the size of inflation lumen 31, a width dimension of inflation lumen 31 that is orthogonal to the dashed line in FIG. 2D may be greater than a height dimension of the lumen 31 (height measured along the dashed line), which creates the non-circular cross-sectional shape of inflation lumen 31, as shown in FIG. 2D. Inflation channel 14 (see FIGS. 2A and 2B) has a circular cross-sectional configuration proximal to support 30. Inflation channel 14 thus includes a transition region 15 (shown in FIGS. 2A and 2B) where channel 14 transitions from the proximal region with the circular cross-sectional configuration to a more distally located region with the non-circular cross-sectional configuration (e.g., oval, elliptical, D-shaped, etc.) In this example, the configuration of channel 14 transitions from a circular cross-sectional configuration to an oval or elliptical cross-sectional configuration, as shown.

Inflation channel 14 is configured and adapted to allow balloon inflation fluid (e.g., liquid/gas) to be advanced therethrough. Inflation channel 14 preferably does not collapse in response to agent delivery through agent delivery lumen 18. Additionally, the material of inflation channel 14 may preferably be able to withstand any chemicals that might be delivered through agent delivery lumen 18. Inflation channel 14 may optionally have a support structure therein, such as one or more of a braided or coiled structure, for support.

Proximal end 37 of balloon support 30 and distal end 39 of balloon support 30 are labeled in FIG. 2F. As shown in FIGS. 2F and 2G, the distal end 13 of outer shaft 12 is disposed about marker band 63 and about the proximal end 37 of balloon support 30 (proximal end 37 is also labeled in FIG. 2A), and may be adhered thereto (e.g., with an adhesive). A material such as PTFE may be disposed over or about the location where the distal end 13 axially overlaps with the balloon support 30 to help secure the components together. Outer shaft 12 may be secured to the proximal end of balloon support 30 using a variety of coupling techniques.

Figure 3A:
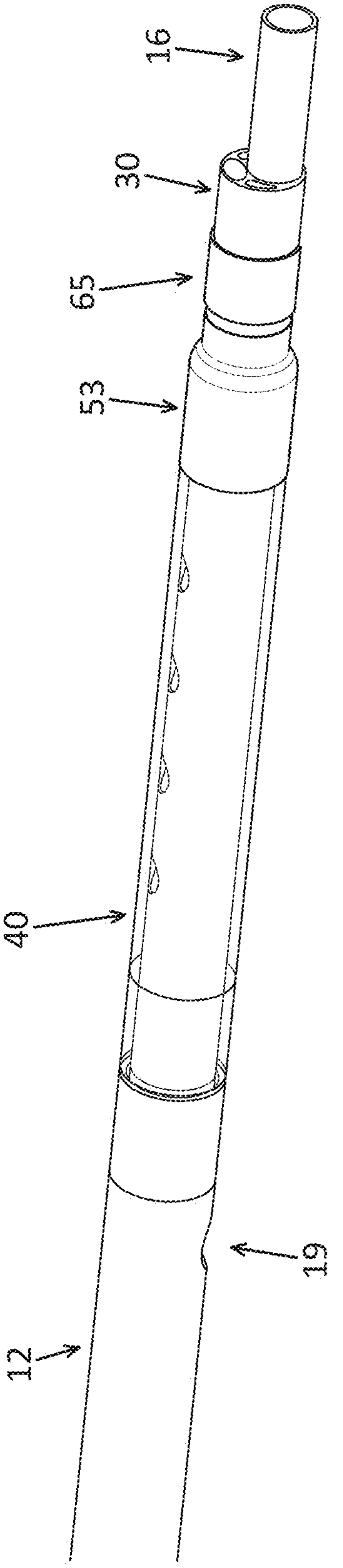
FIGS. 3A and 3B are perspective and side views, respectively, of an exemplary catheter with a balloon that is in a non-expanded configuration.

Catheter 10 may optionally also include marker bands 63 and 65 (in this example there is a proximal marker band 63 as shown in FIG. 2A and a distal mark band 65 as shown in FIG. 3A), which may comprise a radiopaque material to be viewable under radiographic imaging, such as fluoro imaging.

Figure 2J:
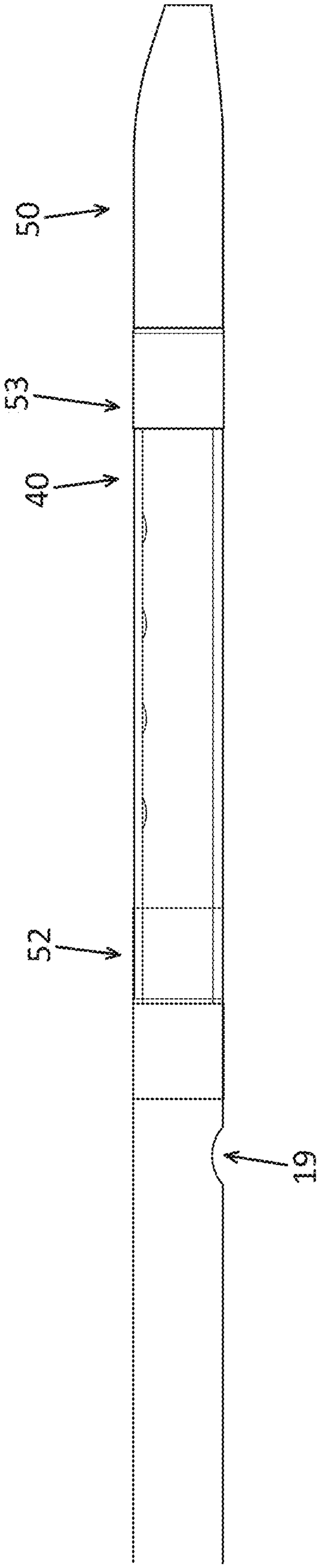

The proximal and distal ends of exemplary balloon 40 may be coupled to and supported by balloon support 30, for example, and may be secured thereto with one or more outer coverings or sheaths. For example, a proximal end of balloon 40 may be secured to support 30 with an outer anchor or retainer 52 (e.g., PTFE material), as shown in FIGS. 2F, 21 and 2J, any of which may be a heat shrunk material, for example. The proximal end of the balloon may be compressed about balloon support 30 and/or it may be adhered thereto (e.g., with an adhesive).

Figure 3B:
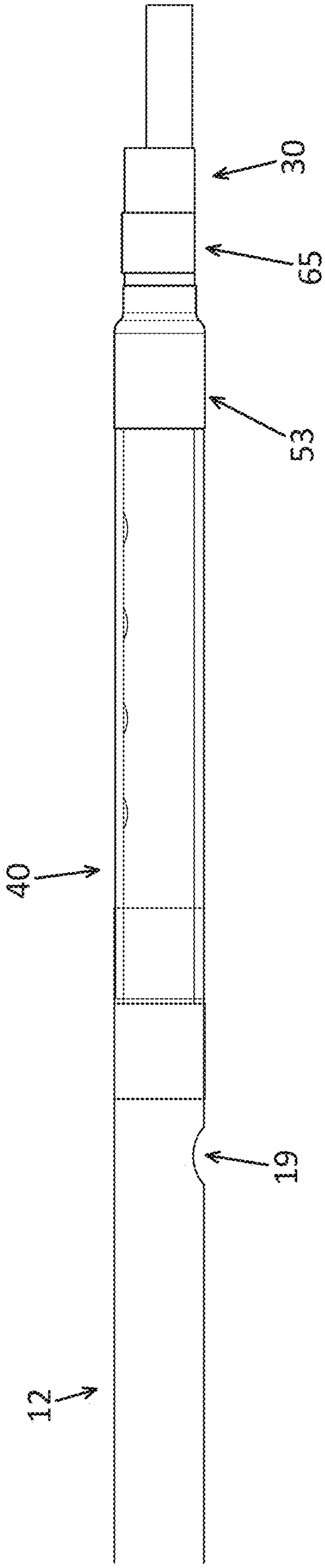

Catheter 10 includes an optional distal marker band 65, which is labeled in FIGS. 3A and 3B (and can be seen in FIG. 2H), which may interface with distal tip 50, as can be seen in FIG. 2H. Tip 50 axially overlaps with marker band 65 to some extent.

FIGS. 3A and 3B illustrate an alternative catheter (which may include any of the features of catheter 10, and vice versa) with a distal balloon anchor or retainer 53 (e.g., PTFE) disposed about the distal end of balloon 40 and balloon support 30. All other reference label in FIGS. 3A and 3B may be referencing the same component that is described herein in other examples or embodiments.

Figure 4A:
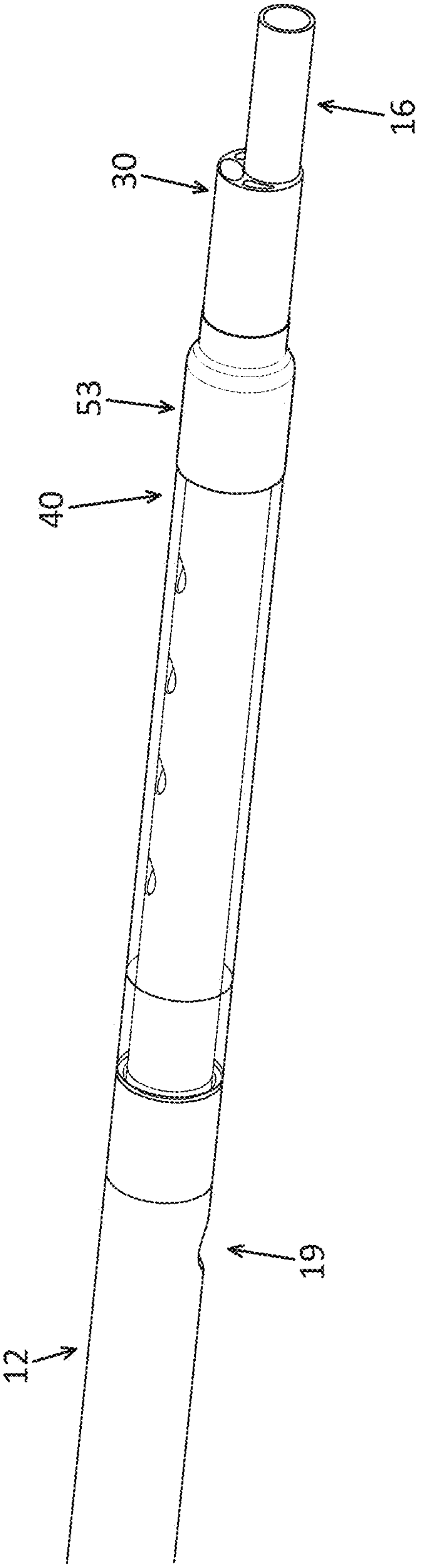
FIGS. 4A and 4B are perspective and side views, respectively, of an exemplary catheter with a balloon that is in a non-expanded configuration.
Figure 4B:
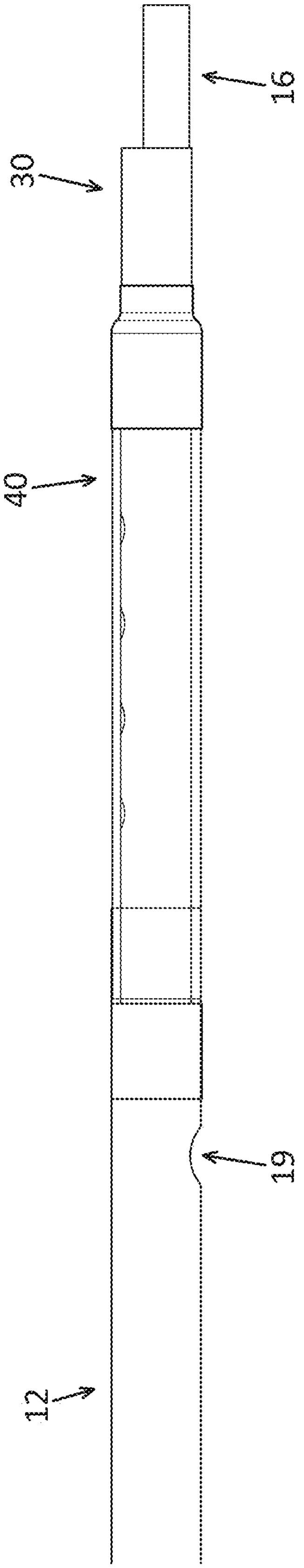
Figure 4C:
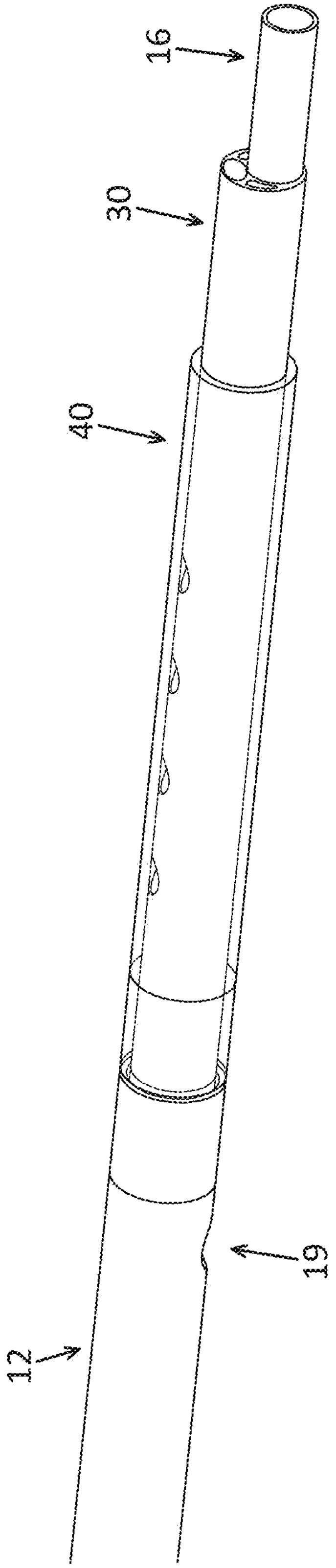
FIGS. 4C and 4D illustrate the catheter from FIGS. 4A and 4B without a distal balloon retaining element.
Figure 4D:
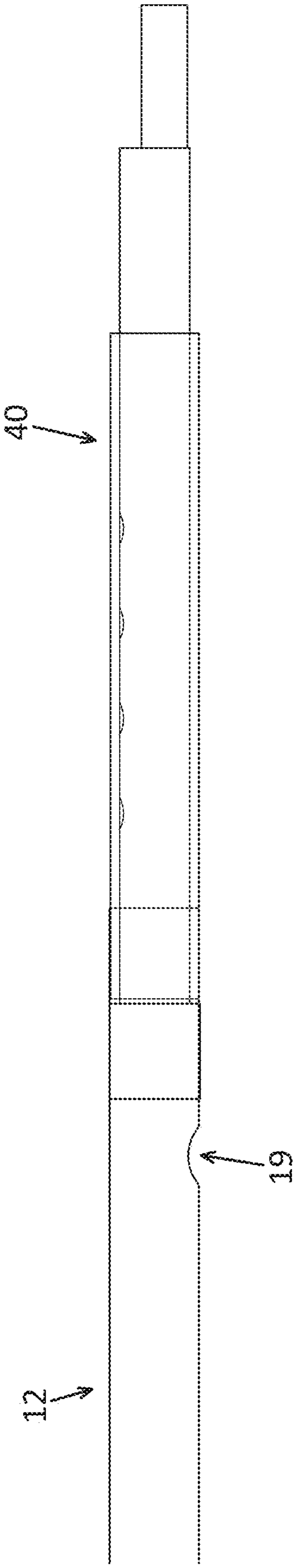

FIGS. 4A-4D illustrate the same catheter as shown in FIGS. 3A and 3B without the optional distal marker band 65. FIGS. 4C and 4D provide an illustration without retainer 53. All other reference labels in FIGS. 4A and 4B may be referencing the same component that is described herein in other examples or embodiments.

Figure 5A:
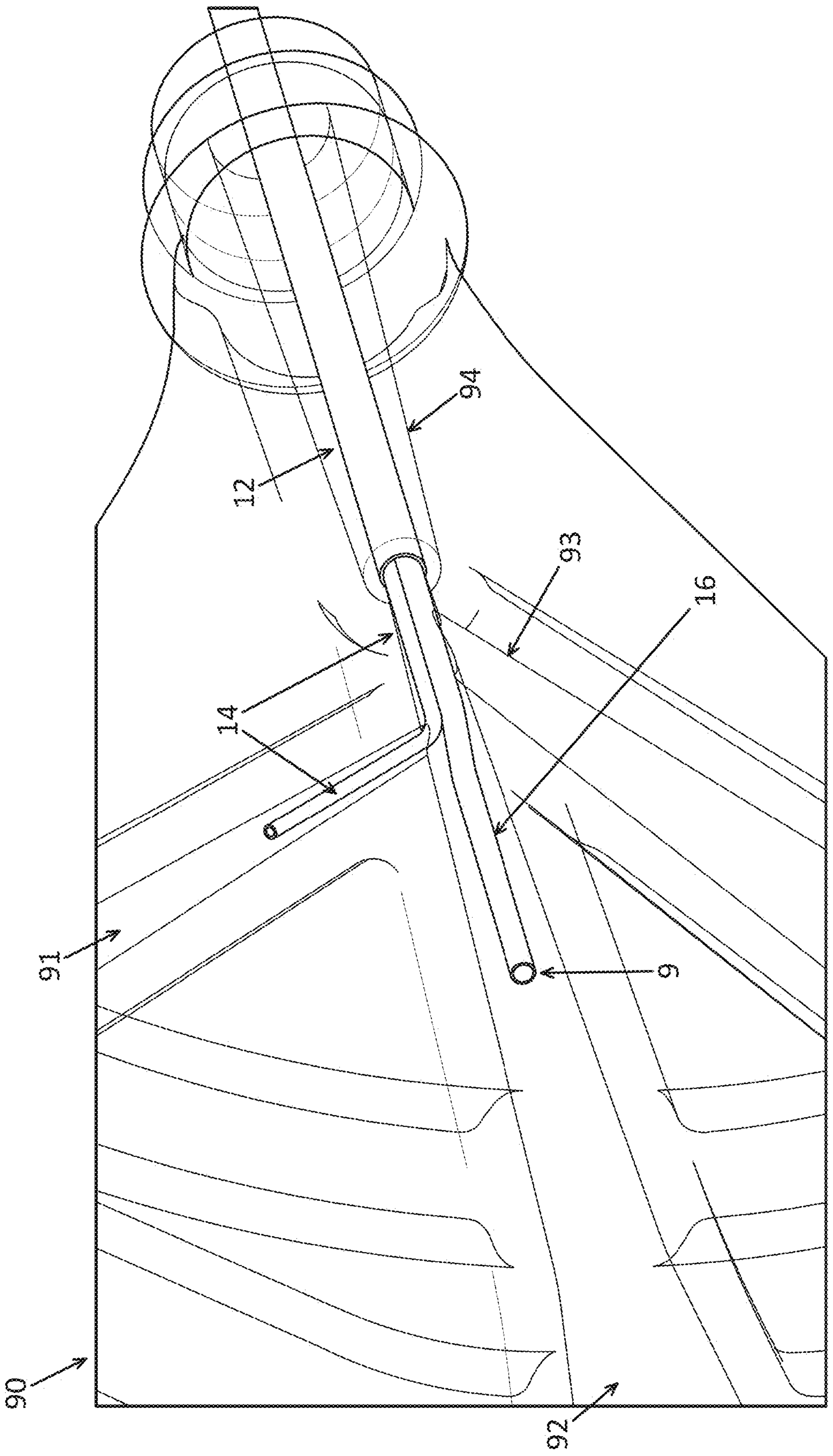
FIGS. 5A and 5B illustrate an exemplary hub of an exemplary catheter that includes at least one deformable lumen.
Figure 5B:
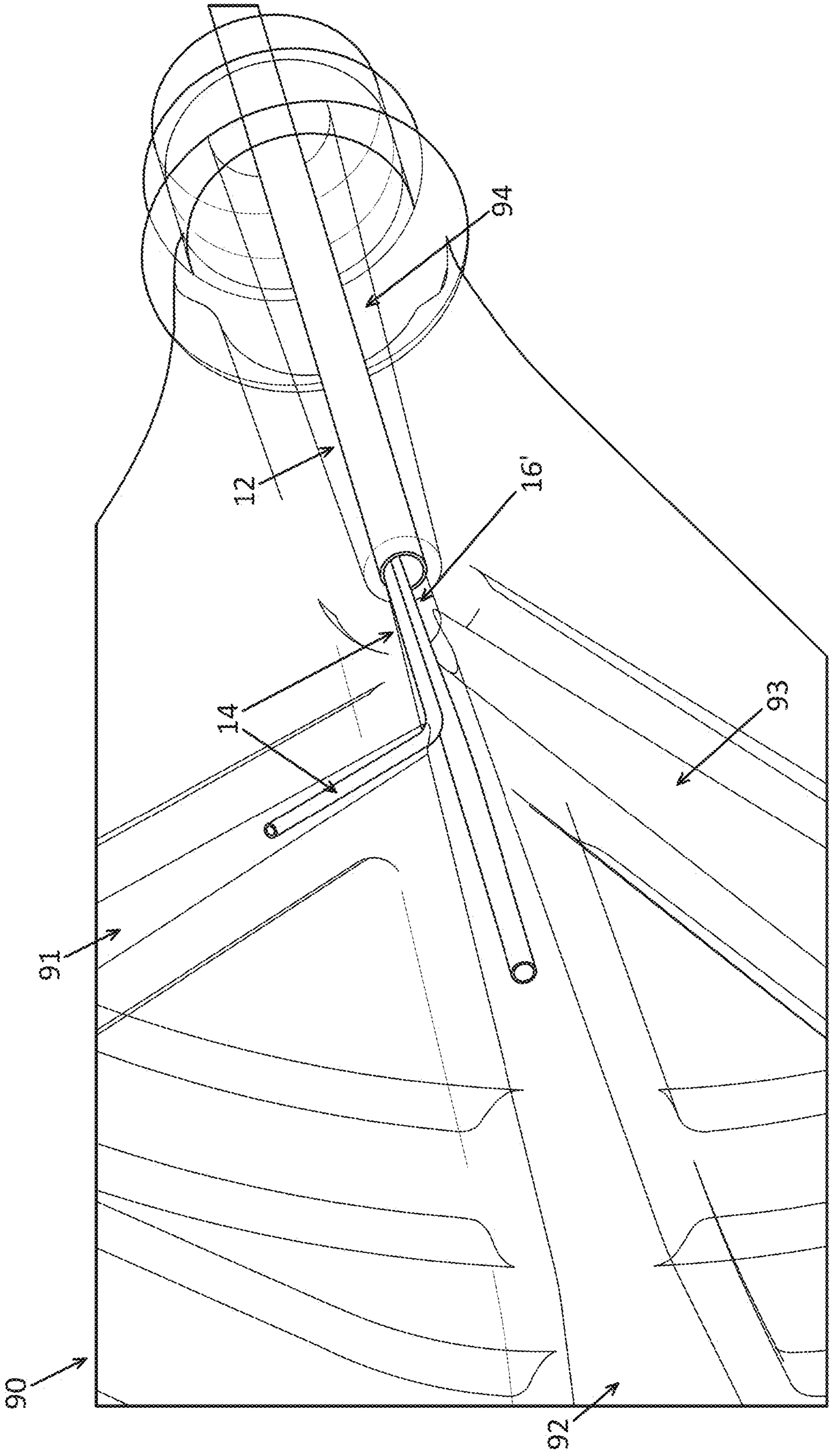

FIGS. 5A and 5B illustrate a portion of a proximal region of the catheter 10 including hub 90, wherein FIG. 5B illustrate a proximal portion of guidewire channel 16' in a collapsed configuration (which may be a biased, at-rest configuration, or which may be deformed from an at-rest configuration). FIG. 5A illustrates guidewire channel 16 in an open, or non-collapsed, configuration. Hub 90 includes three inlet ports, as shown.

Hub 90 includes hub inflation channel or port 91 that is configured to deliver inflation fluid to the proximal end of inflation channel 14. The proximal end of inflation channel 14 is disposed and secured within hub inflation channel or port 91 (optionally with an adhesive), as shown.

Hub 90 also includes hub guidewire channel or port 92, through which a guidewire may be advanced and into the proximal end 9 of the guidewire channel 16. The proximal end 9 of guidewire channel 16 is disposed and secured within hub guidewire channel or port 92, as shown (optionally with an adhesive).

Hub 90 also includes hub agent delivery channel or port 93, into which the one or more agents may be delivered and into agent delivery lumen 18 (see FIGS. 1A, 1B, 1C, 2F, 2G, for example). Potential agents as used herein include contrast agent used to visualize the catheter during the procedure, as well as other agents such as drugs Hub 90 also includes hub distal channel 94 that defines a lumen, into which outer shaft 12 extends and is secured therein (optionally with an adhesive).

In this example, the proximal end regions of inflation channel 14 and guidewire channel 16 are attached to hub 90, and more distally-located regions of inflation channel 14 and guidewire channel 16 are secured (e.g., adhered) to the inflation balloon support 30. Channels 14 and 16 are optionally not coupled to anything else (e.g., are free floating) in between the locations where they are proximally and distally secured. In alternative embodiments, inflation channel 14 and guidewire channel 16 may be coupled together (e.g., with an adhesive) at one or more discrete locations if desired to stabilize the channels relative to each other.

Preferably, guidewire channel 16 is not adapted to elongate or stretch, which may cause the guidewire channel to fold and create an obstruction for the guidewire.

Any of the guidewire channels herein may optionally be a single, monolithic structure from end to end, or they may be as assembly of more than one component.

During assembly, outer shaft 12 may be fed into hub distal channel 94. Inflation channel 14 and guidewire channel 16 may be fed through outer shaft 12 and into their respective hub channels/ports.

In an alternative to the balloon support 30 shown herein, the balloon support may extend all the way proximally toward the hub, or at least extends much further proximally within the outer shaft.

Figure 6A:
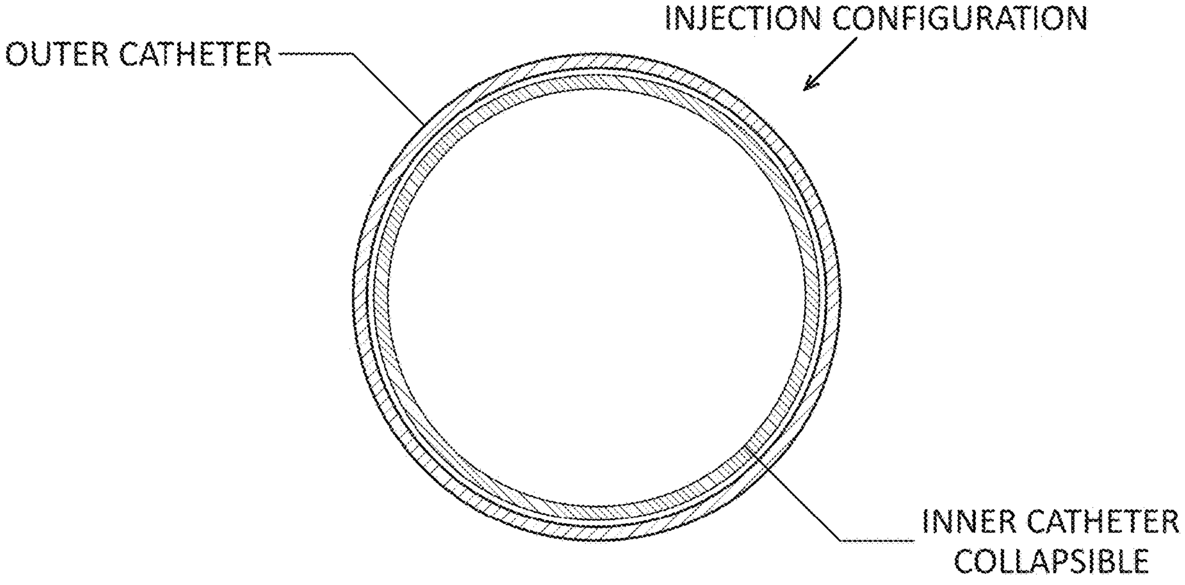
FIGS. 6A and 6B are sectional views of an exemplary catheter than includes at least one deformable lumen.
Figure 6B:
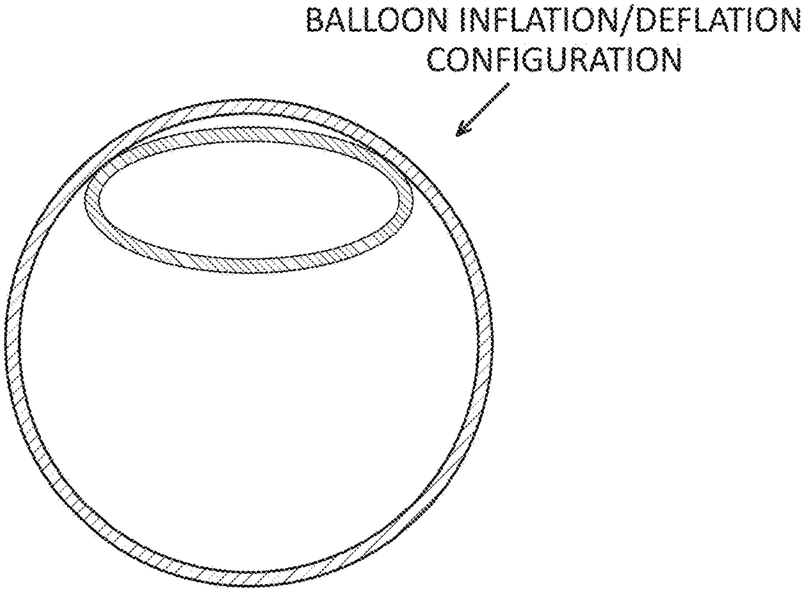

While FIGS. 1A-5B illustrate some features of particular examples, concepts herein may be integrated into other types of catheters. For example, a deformable guidewire channel may be incorporated into any of the catheters described in U.S. Pat. No. 9,550,046; US 2020/0023170; U.S. Pat. No. 10,350,382; and US 2020/0030577. For example, catheters in these references may include co-axial lumens, wherein an outer lumen is an inflation lumen, and wherein an inner lumen is a guidewire/drug delivery lumen. Catheters in these references may include an inner shaft (which may be referred to therein as an inner catheter) and an outer shaft (which may be referred to therein as an outer catheter). It may be desirable for the drug delivery lumen to be as large as possible to facilitate drug delivery while minimizing particle clumping and sticking together. As such, in alternative, modified, designs to those described in these references, the guidewire channel (defining a central guidewire lumen therein) may be sized to occupy all or substantially all of the outer inflation lumen for agent delivery, an example of which is shown in FIG. 6A. FIGS. 6A and 6B illustrate a cross section of a modification to the catheters in the referenced materials, wherein the cross section is taken at a location proximal to the inflatable balloon. FIG. 6A illustrates an outer catheter or outer shaft and an inner catheter or inner shaft, wherein the inner catheter is shown in an open, neutral, configuration. Inner catheter shaft in this example is deformable such that it can collapsed to the collapsed configuration shown in FIG. 6B. When the balloon is inflated or deflated, the guidewire/agent lumen that is defined by the inner shaft can be collapsed (as shown in FIG. 6B) to allow balloon inflation fluid to flow to the balloon or be removed from the balloon through the space/volume defined between the inner surface of outer catheter and the outer surface of the inner catheter. In this manner, the deformable guidewire channel concepts herein may be incorporated into any the catheters described in these references that are incorporated by reference. For example, any of the deformable concepts related to deformable guidewire channels/lumens herein may be applied to the catheter shown in the illustrative design in FIGS. 6A and 6B and to any of the catheters in the disclosures of the references that are incorporated by reference herein.

In some exemplary methods of use, the method includes removing a guidewire from a guidewire lumen. The guidewire channel may be biased and configured to collapse upon removal of the guidewire and/or the guidewire channel may be configured to deform and collapse in response to delivery of an agent through an agent delivery lumen 18 (described elsewhere herein).

In some methods of use, however, it may not be as important to create a agent delivery lumen that is as large as possible. For example, if the agent being delivered is a liquid without particles, it may not be as important to collapse the guidewire channel. In these examples, the guidewire may be left in place in the guidewire channel while delivering the agent out of port(s) 19. Additionally, part of a procedure may include delivering contrast agent into the patient out of port 19, and the guidewire may optionally be left in the guidewire channel during this step. In any of these examples, the guidewire channel may be adapted such that none of the guidewire channel is adapted to be deformable, but the agent port may be proximal to the balloon.

Any of the agents herein may be one or more of fluids (e.g., liquid, gas) or gels, for example.

In alternative embodiments, the catheters herein may be configured with a plurality of separate agent delivery channels/lumens therein, and each agent delivery channel/lumen may be in fluid communication with dedicated one or more agent ports.

The invention claimed is:

1. A catheter for delivering an agent into a patient, the catheter comprising:

an outer shaft comprising one or more agent delivery ports;

a guidewire channel within the outer shaft, the guidewire channel defining a guidewire lumen sized and configured to receive a guidewire in the guidewire lumen;

a balloon inflation channel within the outer shaft, the balloon inflation channel defining a balloon inflation lumen in fluid communication with an internal volume of an inflatable balloon; and an agent delivery lumen defined by an inner surface of the outer shaft, an outer surface of the guidewire channel and an outer surface of the balloon inflation channel, the agent delivery lumen in communication with the one or more agent delivery ports, and the one or more agent delivery ports proximal to at least a portion of the inflatable balloon, and wherein a proximal portion of the guidewire channel is deformable between an open guidewire configuration and a collapsed, agent-delivery configuration.

2. The catheter of claim 1, wherein the proximal portion of the guidewire channel is biased to the collapsed, agent-delivery configuration.

3. The catheter of claim 1, wherein the proximal portion of the guidewire channel is adapted to deform towards the collapsed, agent-delivery configuration in response to an increase in fluid pressure in the agent delivery lumen.

4. The catheter of claim 1, wherein the open guidewire configuration is a circular cross-sectional configuration, and the collapsed, agent-delivery configuration is not a circular cross-sectional configuration.

5. The catheter of claim 1, wherein the guidewire lumen, in a cross-section transverse to a long axis of the catheter and through the proximal portion of the guidewire channel, has an area when the guidewire channel is in the open guidewire configuration that is greater than an area when the guidewire channel is in the collapsed, agent-delivery configuration.

6. The catheter of claim 1, wherein the agent delivery lumen, in a cross-section transverse to a long axis of the catheter and through the proximal portion of the guidewire channel, has an area when the guidewire channel is in the open guidewire configuration that is less than an area when the guidewire channel is in the collapsed, agent-delivery configuration.

7. The catheter of claim 1, wherein the agent delivery lumen has a greater volume when the guidewire channel is in the collapsed, agent-delivery configuration than when the guidewire channel is in the open guidewire configuration.

8. The catheter of claim 1, wherein the guidewire channel is not adapted to collapse in a distal region that extends within the inflatable balloon.

9. The catheter of claim 1, further comprising a balloon support coupled to the balloon inflation channel, the balloon support comprising one or more balloon inflation ports in fluid communication with the balloon inflation lumen and the internal volume of the inflatable balloon to facilitate inflation of the inflatable balloon.

10. The catheter of claim 9, wherein the balloon inflation channel has a distal end that is disposed within a first lumen defined by the balloon support, the first lumen in fluid communication with the one or more balloon inflation ports.

11. The catheter of claim 10, wherein the first lumen has a non-circular cross-sectional configuration.

12. The catheter of claim 10, wherein the balloon inflation channel has a first cross-sectional configuration in a first portion that is proximal to the inflatable balloon that is circular, and wherein the balloon inflation channel has a second cross-sectional configuration in a second portion within the first lumen that is non-circular.

13. The catheter of claim 1, further comprising a balloon support that includes a support lumen extending through the balloon support, at least a portion of the guidewire channel is disposed within the support lumen.

14. The catheter of claim 13, wherein the guidewire channel extends through the support lumen and at least to a distal end of the support lumen.

15. The catheter of claim 1, wherein the outer shaft is secured to a proximal end of a balloon support, and wherein the balloon is secured to the inflatable balloon support.

16. The catheter of claim 15, wherein the balloon support is adapted to prevent elongation of the ballon support to thereby prevent elongation of the inflatable balloon.

17. The catheter of claim 16, wherein the inflatable balloon support comprises one or more strengthening elements to prevent the elongation of the inflatable balloon.

18. The catheter of claim 1, further comprising a balloon support, wherein the guidewire channel is secured to the balloon support thereby preventing a distal portion of the guidewire channel from collapsing within the balloon support.

19. The catheter of claim 1, wherein the proximal portion of the guidewire channel is biased to the open guidewire configuration.

* * * * *